United States Patent
Shanley

(10) Patent No.: US 6,527,799 B2
(45) Date of Patent: Mar. 4, 2003

(54) EXPANDABLE MEDICAL DEVICE WITH DUCTILE HINGES

(75) Inventor: John F. Shanley, Redwood City, CA (US)

(73) Assignee: Conor MedSystems, Inc., Menlo Park, CA (US)

( * ) Notice: Subject to any disclaimer, the term of this patent is extended or adjusted under 35 U.S.C. 154(b) by 0 days.

(21) Appl. No.: 09/932,093

(22) Filed: Aug. 20, 2001

(65) Prior Publication Data

US 2002/0013619 A1 Jan. 31, 2002

Related U.S. Application Data

(60) Division of application No. 09/315,892, filed on May 20, 1999, now Pat. No. 6,293,967, which is a continuation-in-part of application No. 09/183,555, filed on Oct. 29, 1998, now Pat. No. 6,241,762.

(51) Int. Cl.⁷ .................................................. A61C 2/00
(52) U.S. Cl. ..................................... 623/1.15; 623/1.35
(58) Field of Search ............................. 623/1.15, 1.3, 623/1.31, 1.16, 1.17, 1.35; 606/190, 194, 195

(56) References Cited

U.S. PATENT DOCUMENTS

| | | |
|---|---|---|
| 3,657,744 A | 4/1972 | Ersek |
| 4,300,244 A | 11/1981 | Bukros |
| 4,531,936 A | 7/1985 | Gordon |
| 4,542,025 A | 9/1985 | Tice et al. |
| 4,580,568 A | 4/1986 | Gianturco |
| 4,650,466 A | 3/1987 | Luther |
| 4,733,665 A | 3/1988 | Palmaz |
| 4,739,762 A | 4/1988 | Palmaz |
| 4,776,337 A | 10/1988 | Palmaz |
| 4,800,882 A | 1/1989 | Gianturco |
| 4,824,436 A | 4/1989 | Wollnsky |
| 4,834,755 A | 5/1989 | Silvestrini et al. |
| 4,955,878 A | 9/1990 | See et al. |

(List continued on next page.)

FOREIGN PATENT DOCUMENTS

| | | |
|---|---|---|
| EP | 0 335 341 | 10/1989 |
| EP | 0 353 341 | 2/1990 |
| EP | 0375 520 | 6/1990 |

(List continued on next page.)

OTHER PUBLICATIONS

U.S. patent application Ser. No. 09/867,382, Shanley, filed May 31, 2001.

Emanelsson, H., et al., *The Jostent Coronary Stent Range*, Ch. 19.

Primary Examiner—Cary E. O'Connor
(74) Attorney, Agent, or Firm—Burns, Doane, Swecker & Mathis, LLP

(57) ABSTRACT

An expandable tissue supporting device of the present invention employs ductile hinges at selected points in the expandable device. When expansion forces are applied to the device as a whole, the ductile hinges concentrate expansion stresses and strains in small well defined areas. The expandable tissue supporting device includes a plurality of elongated beams arranged in a cylindrical device and connected together by a plurality of ductile hinges. Although many ductile hinge configurations are possible, the ductile hinges preferably have a substantially constant hinge cross sectional area which is smaller than a beam cross sectional area such that as the device is expanded from a first diameter to a second diameter, the ductile hinges experience plastic deformation while the beams are not plastically deformed. The expandable tissue supporting device can be provided with segments which may be expanded in a specified sequence and/or framed hole features for accommodating bifurcations.

19 Claims, 13 Drawing Sheets

U.S. PATENT DOCUMENTS

| | | |
|---|---|---|
| 4,957,508 A | 9/1990 | Kaneko et al. |
| 4,960,790 A | 10/1990 | Steela et al. |
| 4,969,458 A | 11/1990 | Witktor |
| 4,989,601 A | 2/1991 | Marchosky et al. |
| 4,990,155 A | 2/1991 | Wilkoff et al. |
| 4,994,071 A | 2/1991 | MacGregor |
| 5,019,090 A | 5/1991 | Pinchuk |
| 5,049,132 A | 9/1991 | Shaffer et al. |
| 5,053,048 A | 10/1991 | Pinchuk |
| 5,059,166 A | 10/1991 | Fischell et al. |
| 5,059,178 A | 10/1991 | Ya et al. |
| 5,059,211 A | 10/1991 | Stack et al. |
| 5,078,726 A | 1/1992 | Kreamer |
| 5,092,841 A | 3/1992 | Spears |
| 5,102,417 A | 4/1992 | Palmaz |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,286,254 A | 2/1994 | Shapland et al. |
| 5,292,512 A | 3/1994 | Schaefer et al. |
| 5,304,121 A | 4/1994 | Sahatjian |
| 5,314,688 A | 5/1994 | Kauffman et al. |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narcisco, Jr. |
| 5,439,446 A | 8/1995 | Barry |
| 5,439,686 A | 8/1995 | Desai et al. |
| 5,441,515 A | 8/1995 | Khosravi et al. |
| 5,441,745 A | 8/1995 | Presant et al. |
| 5,443,496 A | 8/1995 | Schwartz et al. |
| 5,443,497 A | 8/1995 | Venbrx |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,473,055 A | 12/1995 | Mongelli et al. |
| 5,499,373 A | 3/1996 | Richards et al. |
| 5,523,092 A | 6/1996 | Hanson et al. |
| 5,545,210 A | 8/1996 | Hess et al. |
| 5,556,413 A | 9/1996 | Lam |
| 5,575,771 A | 11/1996 | Walinsky |
| 5,578,075 A | 11/1996 | Dayton |
| 5,593,434 A | 1/1997 | Williams |
| 5,607,442 A | 3/1997 | Fischell et al. |
| 5,616,608 A | 4/1997 | Kinsella et al. |
| 5,617,878 A | 4/1997 | Taheri |
| 5,618,299 A | 4/1997 | Khosravi et al. |
| 5,628,787 A | 5/1997 | Mayer |
| 5,643,314 A | 7/1997 | Carpenter et al. |
| 5,674,278 A | 10/1997 | Boneau |
| 5,697,971 A | 12/1997 | Fischell et al. |
| 5,707,385 A | 1/1998 | Williams |
| 5,713,949 A | 2/1998 | Jayaranman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,741,293 A | 4/1998 | Wijay |
| 5,759,192 A | 6/1998 | Saunders |
| 5,766,239 A | 6/1998 | Cox |
| 5,769,883 A | 6/1998 | Buscemi et al. |
| 5,776,181 A | 7/1998 | Lee et al. |
| 5,817,152 A | 10/1998 | Birdsall et al. |
| 5,824,045 A | 10/1998 | Alt |
| 5,824,049 A | 10/1998 | Ragheb et al. |
| 5,827,322 A | 10/1998 | Williams |
| 5,837,313 A | 11/1998 | Ding et al. |
| 5,843,117 A | 12/1998 | Alt et al. |
| 5,843,120 A | 12/1998 | Israel et al. |
| 5,843,175 A | 12/1998 | Frantzen |
| 5,853,419 A | 12/1998 | Imran |
| 5,855,600 A | 1/1999 | Alt |
| 5,868,781 A | 2/1999 | Killion |
| 5,873,904 A | 2/1999 | Ragheb et al. |
| 5,876,419 A | 3/1999 | Carpenter et al. |
| 5,886,026 A | 3/1999 | Hunter et al. |
| 5,922,020 A * | 7/1999 | Klein et al. ................ 606/194 |
| 5,922,021 A | 7/1999 | Jang |
| 5,964,798 A | 10/1999 | Imran |
| 5,968,092 A | 10/1999 | Buxcemi et al. |
| 5,972,027 A | 10/1999 | Johnson |
| 5,976,182 A | 11/1999 | Cox |
| 5,984,957 A | 11/1999 | Laptewicz, Jr. et al. |
| 6,007,517 A | 12/1999 | Anderson |
| 6,017,363 A | 1/2000 | Hojeibane |
| 6,019,789 A | 2/2000 | Dinh et al. |
| 6,022,371 A | 2/2000 | Killion |
| 6,030,414 A | 2/2000 | Taheri |
| 6,042,606 A | 3/2000 | Frantzen |
| 6,056,722 A | 5/2000 | Jayaraman |
| 6,063,101 A | 5/2000 | Jacobsen et al. |
| 6,083,258 A | 7/2000 | Yadav |
| 6,096,070 A | 8/2000 | Ragheb et al. |
| 6,099,561 A | 8/2000 | Alt |
| 6,120,535 A | 9/2000 | McDonald et al. |
| 6,156,062 A | 12/2000 | McGuinness |
| 6,174,326 B1 | 1/2001 | Kitaoka et al. |
| 6,193,746 B1 | 2/2001 | Strecker |
| 6,206,914 B1 | 3/2001 | Soykan et al. |
| 6,206,915 B1 | 3/2001 | Fagan et al. |
| 6,206,916 B1 | 3/2001 | Furst |
| 6,240,616 B1 | 6/2001 | Yan |
| 6,241,762 B1 | 6/2001 | Shanley |
| 6,249,952 B1 | 6/2001 | Ding |
| 6,273,910 B1 | 8/2001 | Limon |
| 6,273,913 B1 | 8/2001 | Wright et al. |
| 6,280,411 B1 | 8/2001 | Lennox |
| 6,290,673 B1 | 9/2001 | Shanley |
| 6,293,967 B1 | 9/2001 | Shanley |
| 6,309,414 B1 | 10/2001 | Rolando et al. |
| 6,395,326 B1 | 5/2002 | Castro et al. |
| 2001/0000802 A1 | 5/2001 | Soykan et al. |
| 2001/0027340 A1 | 10/2001 | Wright et al. |
| 2001/0044648 A1 | 11/2001 | Wolinsky et al. |
| 2002/0007209 A1 | 1/2002 | Scheerder et al. |
| 2002/0022876 A1 | 2/2002 | Richter et al. |

FOREIGN PATENT DOCUMENTS

| | | |
|---|---|---|
| EP | 0470 569 | 2/1992 |
| EP | 0566 245 | 10/1993 |
| EP | 0567 816 | 11/1993 |
| EP | 0627 226 | 12/1994 |
| EP | 0679 373 | 11/1995 |
| EP | 0734 698 | 10/1996 |

| | | | | | | |
|---|---|---|---|---|---|---|
| EP | 0706 376 | 6/1997 | | WO | WO 95/03795 | 2/1995 |
| EP | 0897 700 | 2/1999 | | WO | WO 96/03092 | 2/1996 |
| EP | 0 950 386 | 10/1999 | | WO | WO 96/29028 | 9/1996 |
| FR | 2 764 794 | 12/1998 | | WO | WO 96/32907 | 10/1996 |
| WO | WO 90/13332 | 11/1990 | | WO | WO 97/04721 | 2/1997 |
| WO | WO 91/10424 | 7/1991 | | WO | WO 98/18407 | 5/1998 |
| WO | WO 91/11193 | 8/1991 | | WO | WO 98/19628 | 5/1998 |
| WO | WO 91/12779 | 9/1991 | | WO | WO 98/23228 | 6/1998 |
| WO | WO 92/12717 | 8/1992 | | WO | WO 98/58600 | 12/1998 |
| WO | WO 92/15286 | 9/1992 | | WO | WO 99/15108 | 4/1999 |
| WO | WO 93/06792 | 4/1993 | | WO | WO 99/49928 | 10/1999 |
| WO | WO 94/21308 | 9/1994 | | WO | WO 00/45744 | 8/2000 |
| WO | WO 94/24961 | 11/1994 | | | | |
| WO | WO 95/03036 | 2/1995 | | | | |

* cited by examiner

EXPANDABLE MEDICAL DEVICE WITH DUCTILE HINGES

This application is a divisional of application Ser. No. 09/315,892, filed on May 20, 1999 now U.S. Pat. No. 6,293,967, which is a continuation-in-part of application Ser. No. 09/183,555, filed on Oct. 29, 1998, now U.S. Pat. No. 6,241,762.

BACKGROUND OF THE INVENTION

1. Field of the Invention

The present invention relates to tissue-supporting medical devices, and more particularly to expandable, non-removable devices that are implanted within a bodily lumen of a living animal or human to support the organ and maintain patency.

2. Summary of the Related Art

In the past, permanent or biodegradable devices have been developed for implantation within a body passageway to maintain patency of the passageway. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665, 4,739,762, and 4,776,337). Known construction materials for use in stents include polymers, organic fabrics and biocompatible metals, such as, stainless steel, gold, silver, tantalum, titanium, and shape memory alloys such as Nitinol.

U.S. Pat. Nos. 4,733,665, 4,739,762, and 4,776,337 disclose expandable and deformable interluminal vascular grafts in the form of thin-walled tubular members with axial slots allowing the members to be expanded radially outwardly into contact with a body passageway. After insertion, the tubular members are mechanically expanded beyond their elastic limit and thus permanently fixed within the body. The force required to expand these tubular stents is proportional to the thickness of the wall material in a radial direction. To keep expansion forces within acceptable levels for use within the body (e.g., 5–10 atm), these designs must use very thin-walled materials (e.g., stainless steel tubing with 0.0025 inch thick walls). However, materials this thin are not visible on conventional fluoroscopic and x-ray equipment and it is therefore difficult to place the stents accurately or to find and retrieve stents that subsequently become dislodged and lost in the circulatory system.

Further, many of these thin-walled tubular stent designs employ networks of long, slender struts whose width in a circumferential direction is two or more times greater than their thickness in a radial direction. When expanded, these struts are frequently unstable, that is, they display a tendency to buckle, with individual struts twisting out of plane. Excessive protrusion of these twisted struts into the bloodstream has been observed to increase turbulence, and thus encourage thrombosis. Additional procedures have often been required to attempt to correct this problem of buckled struts. For example, after initial stent implantation is determined to have caused buckling of struts, a second, high-pressure balloon (e.g., 12 to 18 atm) would be used to attempt to drive the twisted struts further into the lumen wall. These secondary procedures can be dangerous to the patient due to the risk of collateral damage to the lumen wall.

Many of the known stents display a large elastic recovery, known in the field as "recoil," after expansion inside a lumen. Large recoil necessitates over-expansion of the stent during implantation to achieve the desired final diameter. Over-expansion is potentially destructive to the lumen tissue. Known stents of the type described above experience recoil of up to about 6 to 12% from maximum expansion.

Large recoil also makes it very difficult to securely crimp most known stents onto delivery catheter balloons. As a result, slippage of stents on balloons during interlumenal transportation, final positioning, and implantation has been an ongoing problem. Many ancillary stent securing devices and techniques have been advanced to attempt to compensate for this basic design problem. Some of the stent securing devices include collars and sleeves used to secure the stent onto the balloon.

Another problem with known stent designs is non-uniformity in the geometry of the expanded stent. Non-uniform expansion can lead to non-uniform coverage of the lumen wall creating gaps in coverage and inadequate lumen support. Further, over expansion in some regions or cells of the stent can lead to excessive material strain and even failure of stent features. This problem is potentially worse in low expansion force stents having smaller feature widths and thicknesses in which manufacturing variations become proportionately more significant. In addition, a typical delivery catheter for use in expanding a stent includes a balloon folded into a compact shape for catheter insertion. The balloon is expanded by fluid pressure to unfold the balloon and deploy the stent. This process of unfolding the balloon causes uneven stresses to be applied to the stent during expansion of the balloon due to the folds causing the problem non-uniform stent expansion.

U.S. Pat. No. 5,545,210 discloses a thin-walled tubular stent geometrically similar to those discussed above, but constructed of a nickel-titanium shape memory alloy ("Nitinol"). This design permits the use of cylinders with thicker walls by making use of the lower yield stress and lower elastic modulus of martensitic phase Nitinol alloys. The expansion force required to expand a Nitinol stent is less than that of comparable thickness stainless steel stents of a conventional design. However, the "recoil" problem after expansion is significantly greater with Nitinol than with other materials. For example, recoil of a typical design Nitinol stent is about 9%. Nitinol is also more expensive, and more difficult to fabricate and machine than other stent materials, such as stainless steel.

All of the above stents share a critical design property: in each design, the features that undergo permanent deformation during stent expansion are prismatic, i.e., the cross sections of these features remain constant or change very gradually along their entire active length. To a first approximation, such features deform under transverse stress as simple beams with fixed or guided ends: essentially, the features act as a leaf springs. These leaf spring like structures are ideally suited to providing large amounts of elastic deformation before permanent deformation commences. This is exactly the opposite of ideal stent behavior. Further, the force required to deflect prismatic stent struts in the circumferential direction during stent expansion is proportional to the square of the width of the strut in the circumferential direction. Expansion forces thus increase rapidly with strut width in the above stent designs. Typical expansion pressures required to expand known stents are between about 5 and 10 atmospheres. These forces can cause substantial damage to tissue if misapplied.

FIG. 1 shows a typical prior art "expanding cage" stent design. The stent 10 includes a series of axial slots 12 formed in a cylindrical tube 14. Each axial row of slots 12 is displaced axially from the adjacent row by approximately half the slot length providing a staggered slot arrangement. The material between the slots 12 forms a network of axial struts 16 joined by short circumferential links 18. The cross section of each strut 16 remains constant or varies gradually along the entire length of the strut and thus the rectangular moment of inertia and the elastic and plastic section moduli of the cross section also remain constant or vary gradually along the length of the strut. Such a strut 16 is commonly referred to as a prismatic beam. Struts 16 in this type of design are typically 0.005 to 0.006 inches (0.127–0.1524 mm) wide in the circumferential direction. Strut thicknesses in the radial direction are typically about 0.0025 inches (0.0635 mm) or less to keep expansion forces within acceptable levels. However, most stent materials must be approximately 0.005 inches (0.127 mm) thick for good visibility on conventional fluoroscopic equipment. This high ratio of strut width to thickness, combined with the relatively high strut length and the initial curvature of the stent tubing combine to cause the instability and bucking often seen in this type of stent design. When expanded, the stent structure of FIG. 1 assumes the roughly diamond pattern commonly seen in expanded sheet metal.

Another stent described in PCT publication number WO 96/29028 uses struts with relatively weak portions of locally-reduced cross sections which on expansion of the stent act to concentrate deformation at these areas. However, as discussed above non-uniform expansion is even more of a problem when smaller feature widths and thicknesses are involved because manufacturing variations become proportionately more significant. The locally-reduced cross section portions described in this document are formed by pairs of circular holes. The shape of the locally-reduced cross section portions undesirably concentrates the plastic strain at the narrowest portion. This concentration of plastic strain without any provision for controlling the level of plastic strain makes the stent highly vulnerable to failure.

In view of the drawbacks of the prior art stents, it would be advantageous to be able to expand a stent with an expansion force at a low level independent of choice of stent materials, material thickness, or strut dimensions.

It would further be advantageous to have a tissue-supporting device that permits a choice of material thickness that could be viewed easily on conventional fluoroscopic equipment for any material.

It would also be advantageous to have a tissue-supporting device that is inherently stable during expansion, thus eliminating buckling and twisting of structural features during stent deployment.

It would also be desirable to control strain to a desired level which takes advantage of work hardening without approaching a level of plastic strain at which failure may occur.

In addition, it would be advantageous to have a tissue-supporting device with minimal elastic recovery, or "recoil" of the device after expansion.

It would be advantageous to have a tissue supporting device that can be securely crimped to the delivery catheter without requiring special tools, techniques, or ancillary clamping features.

It would further be advantageous to have a tissue-supporting device that has improved resistance to compressive forces (improved crush strength) after expansion.

It would also be advantageous to have a tissue-supporting device that achieves all the above improvements with minimal foreshortening of the overall stent length during expansion.

Finally, it would also be advantageous to provide a tissue-supporting device which is differentially expandable and/or which has framed hole features for accommodating bifurcations.

SUMMARY OF THE INVENTION

The present invention addresses several important problems in expandable medical device design including: high expansion force requirements; lack of radio-opacity in thin-walled stents; buckling and twisting of stent features during expansion; poor crimping properties; and excessive elastic recovery ("recoil") after implantation. The invention also provides benefits of improved resistance to compressive forces after expansion, control of the level of plastic strain, and low axial shortening during expansion. Some embodiments of the invention also provide improved uniformity of expansion by limiting a maximum geometric deflection between struts. Other embodiments of the invention include segments of the expandable device which may be expanded in a specified sequence and/or framed hole features for accommodating bifurcations.

The invention involves the incorporation of stress/strain concentration features or "ductile hinges" at selected points in the body of an expandable cylindrical medical device. When expansion forces are applied to the device as a whole, these ductile hinges concentrate expansion stresses and strains in small, well-defined areas while limiting strut deflection and plastic strain to specified levels.

In accordance with one aspect of the present invention, an expandable medical device includes a plurality of elongated beams and a plurality of ductile hinges connecting the plurality of beams together in a radially expandable substantially cylindrical device. The plurality of elongated beams have a beam width in a circumferential direction. The ductile hinges have a width in a circumferential direction along a portion of a hinge length which is smaller than the beam width such that as the device is expanded the ductile hinges experience plastic deformation while the beams are not plastically deformed. A first section of the substantially cylindrical device includes ductile hinges having a first width and a second section of the substantially cylindrical device includes ductile hinges having a second width different from the first width such that the first section expands before the second section.

In accordance with a further aspect of the invention, an expandable medical device includes a plurality of elongated beams and a plurality of ductile hinges connecting the plurality of beams together in a radially expandable substantially cylindrical device. The plurality of elongated beams are joined together in a regular pattern to form the substantially cylindrical device. The plurality of elongated beams have a beam width in a circumferential direction and the ductile hinges have a width in a circumferential direction along a portion of a hinge length which is smaller than the beam width such that as the device is expanded the ductile hinges experience plastic deformation while the beams are not plastically deformed. A hole feature interrupts the regular pattern of the plurality of beams, the hole feature accommodating a bifurcation in a vessel.

In accordance with another aspect of the present invention, a method of expanding a medical device includes the steps of:

providing a substantially cylindrical expandable medical device having a first section with ductile hinges of a first configuration and a second section with ductile hinges of a second configuration which requires a different force for expansion than the first configuration; and expanding the device in a controlled expansion sequence with an expandable member.

BRIEF DESCRIPTION OF THE DRAWINGS

The invention will now be described in greater detail with reference to the preferred embodiments illustrated in the accompanying drawings, in which like elements bear like reference numerals, and wherein:

FIGS. 12b and 12c are unexpanded and expanded schematic side views of the tissue supporting device of FIG. 12a.

DETAILED DESCRIPTION OF THE PREFERRED EMBODIMENTS

Figure 1:
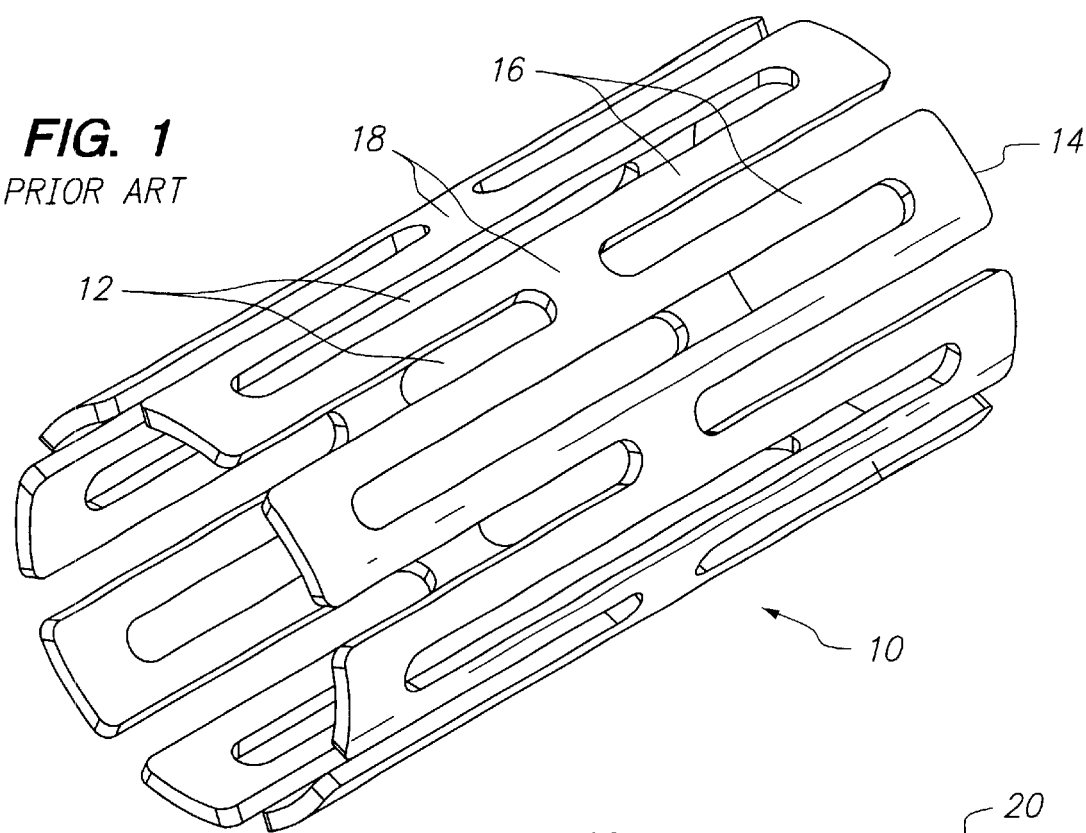
FIG. 1 is an isometric view of a prior art tissue-supporting device.
Figure 2:
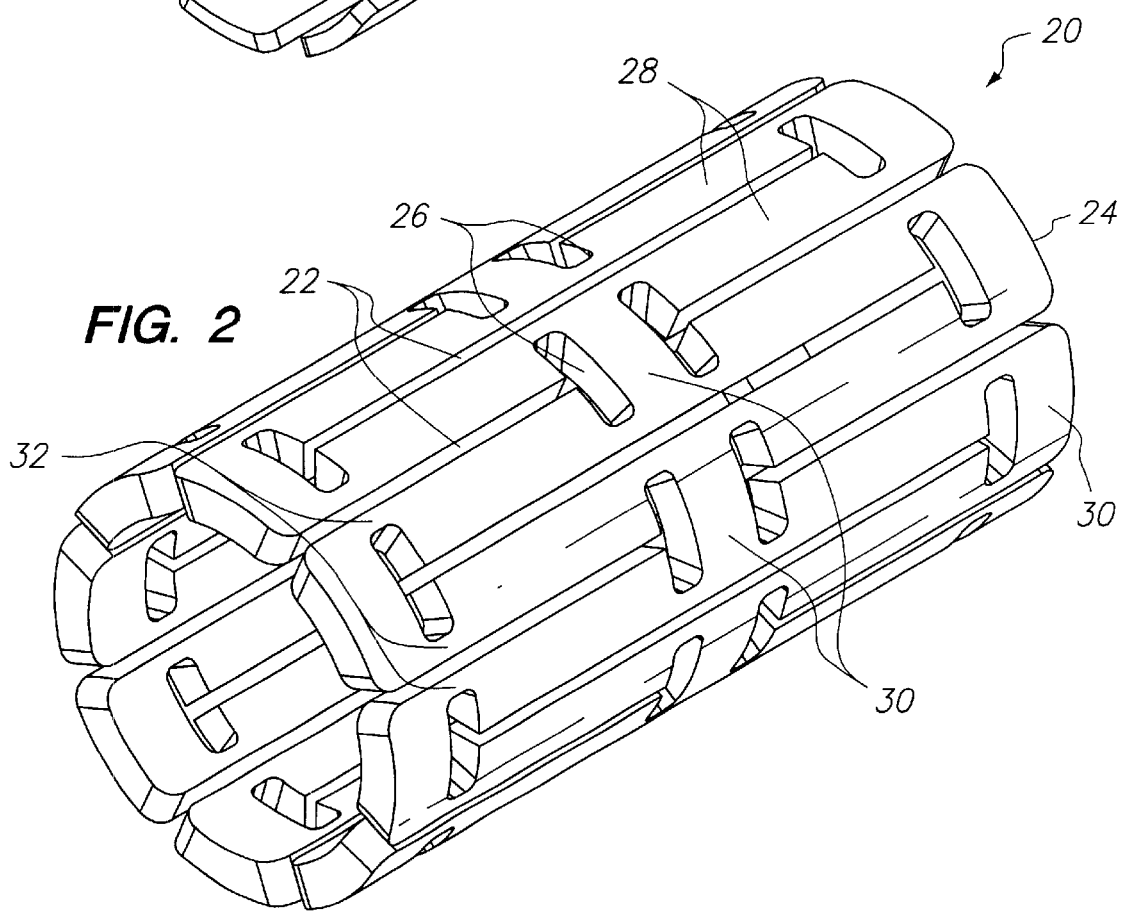
FIG. 2 is an isometric view of a tissue-supporting device in accordance with one embodiment of the invention.

FIG. 2 shows one embodiment of an expandable tissue supporting device 20 in accordance with the present invention. The tissue supporting device 20 includes a series of axial slots 22 formed in a cylindrical tube 24. Each axial slot 22 is displaced axially from the slots in adjacent rows of slots by approximately half the slot length resulting in a staggered slot arrangement. The offset between adjacent rows of slots results in alternate rows of slots which extend to the ends of the cylindrical tube 24. At each interior end of each of the axial slots 22 a circumferential slot 26 is formed. The material between the slots 22 forms a network of axial struts 28 extending substantially parallel to an axis of the tube 24. The axial struts 28 are joined by short circumferential links 30. The circumferential links 30 are positioned at both the interior of the cylindrical tube and at the ends of the cylindrical tube. The cross section (and rectangular moment of inertia) of each of the struts 28 is not constant along the length of the strut. Rather, the strut cross section changes abruptly at both ends of each strut 28 at the location of the circumferential slots 26. The struts 28 are thus not prismatic. Each individual strut 28 is linked to the rest of the structure through a pair of reduced sections 32, one at each end, which act as stress/strain concentration features. The reduced sections 32 of the struts function as hinges in the cylindrical structure. Since the stress/strain concentration features 32 are designed to operate into the plastic deformation range of generally ductile materials, they are referred to as ductile hinges. Such features are also commonly referred to as "Notch Hinges" or "Notch Springs" in ultra-precision mechanism design, where they are used exclusively in the elastic range.

With reference to the drawings and the discussion, the width of any feature is defined as its dimension in the circumferential direction of the cylinder. The length of any feature is defined as its dimension in the axial direction of the cylinder. The thickness of any feature is defined as the wall thickness of the cylinder.

The presence of the ductile hinges 32 allows all of the remaining features in the tissue supporting device to be increased in width or the circumferentially oriented component of their respective rectangular moments of inertia—thus greatly increasing the strength and rigidity of these features. The net result is that elastic, and then plastic deformation commence and propagate in the ductile hinges 32 before other structural elements of the device undergo any significant elastic deformation. The force required to expand the tissue supporting device 20 becomes a function of the geometry of the ductile hinges 32, rather than the device structure as a whole, and arbitrarily small expansion forces can be specified by changing hinge geometry for virtually any material wall thickness. In particular, wall thicknesses great enough to be visible on a fluoroscope can be chosen for any material of interest.

In order to get minimum recoil, the ductile hinges 32 should be designed to operate well into the plastic range of the material, and relatively high local strain-curvatures are developed. When these conditions apply, elastic curvature is a very small fraction of plastic or total curvature, and thus when expansion forces are relaxed, the percent change in hinge curvature is very small. When incorporated into a strut network designed to take maximum advantage of this effect, the elastic springback, or "recoil," of the overall stent structure is minimized.

In the embodiment of FIG. 2, it is desirable to increase the width of the individual struts 28 between the ductile hinges 32 to the maximum width that is geometrically possible for a given diameter and a given number of struts arrayed around that diameter. The only geometric limitation on strut width is the minimum practical width of the slots 22 which is about 0.002 inches (0.0508 mm) for laser machining. Lateral stiffness of the struts 28 increases as the cube of strut width, so that relatively small increases in strut width significantly increase strut stiffness. The net result of inserting ductile hinges 32 and increasing strut width is that the struts 28 no longer act as flexible leaf springs, but act as essentially rigid beams between the ductile hinges. All radial expansion or compression of the cylindrical tissue supporting device 20 is accommodated by mechanical strain in the hinge features 32, and yield in the hinge commences at very small overall radial expansion or compression.

Yield in ductile hinges at very low gross radial deflections also provides the superior crimping properties displayed by the ductile hinge-based designs. When a tissue supporting device is crimped onto a folded catheter balloon, very little radial compression of the device is possible since the initial fit between balloon and device is already snug. Most stents simply rebound elastically after such compression, resulting in very low clamping forces and the attendant tendency for the stent to slip on the balloon. Ductile hinges, however, sustain significant plastic deformation even at the low deflections occurring during crimping onto the balloon, and therefore a device employing ductile hinges displays much higher clamping forces. The ductile hinge designs according to the present invention may be securely crimped onto a balloon of a delivery catheter by hand or by machine without the need for auxiliary retaining devices commonly used to hold known stents in place.

The geometric details of the stress/strain concentration features or ductile hinges 32 can be varied greatly to tailor the exact mechanical expansion properties to those required in a specific application. The most obvious and straightforward ductile hinges are formed by slots or notches with rounded roots, as in FIGS. 3a and 3c. Since the laser beams often used to fabricate these features are themselves round, slots or notches with circular roots are also among the easiest to fabricate.

Figure 3A:
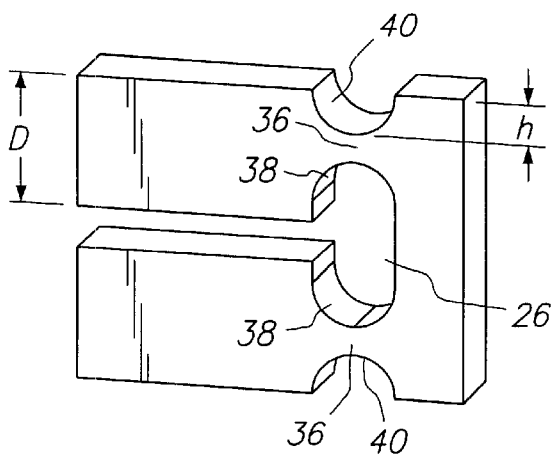
FIGS. 3a–d are perspective views of ductile hinges according to several variations of the invention.

FIG. 3a shows a ductile hinge 36 formed by a pair of opposed circular grooves 38, 40. According to this embodiment the circumferential slot 26 has semicircular ends 38 having a radius of curvature r. Outer semicircular grooves 40 opposed the semicircular ends 38 and also have a radius of curvature r. FIG. 3c shows another ductile hinge 54 formed by a parabolic groove 56.

Generally, the ductile hinges 36 of the embodiment of FIG. 3a formed between pairs of concave curves 38, 40 have a minimum width along a line connecting their respective centers of curvature. When the struts connected by the ductile hinge are moved apart or together, plastic deformation is highly concentrated in a region immediately adjacent to the plane that bisects the hinge at this narrow point.

For smaller deflection, this very high strain concentration at the bisecting plane is acceptable, and in some cases, useful. For stent crimping purposed, for example, it is desirable to generate relatively large plastic deformations at very small deflection angles.

As a practical matter, however, strut deflection angles for device expansion are often in the 25° to 45° range. At these angles, strain at the root or bisecting plane of concave ductile hinge features can easily exceed the 50 to 60% elongation-to-failure of 316L stainless steel, one of the most ductile stent materials. Deflection limiting features which will be described further below limit the geometric deflection of struts, but these features do not in themselves affect the propagation pattern of plastic deformation in a given ductile hinge design. For concave ductile hinges at large bend angles, very high strain concentrations remain. Scanning electron micrographs have confirmed this analysis.

In many engineering applications, it is desirable to limit the amount of strain, or "cold-work," in a material to a specified level in order to optimize material properties and to assure safe operation. For example, in medical applications it is desirable to limit the amount of cold-work in 316L stainless steel to about 30%. At this level, the strength of the material is increased, while the material strain is still well below the failure range. Ideally, therefore, a safe and effective ductile hinge should not simply limit gross deflection, but reliably limit material strain to a specified level.

Figure 3B:
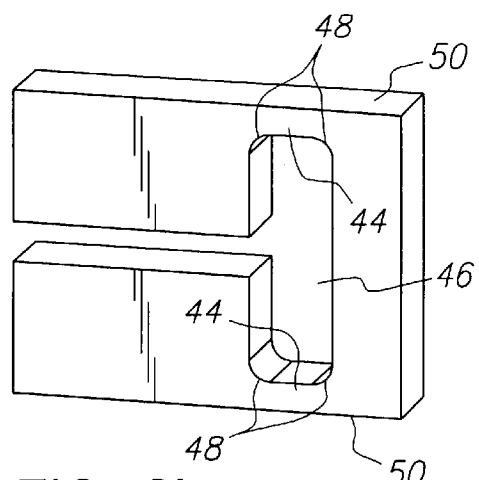
Figure 3C:
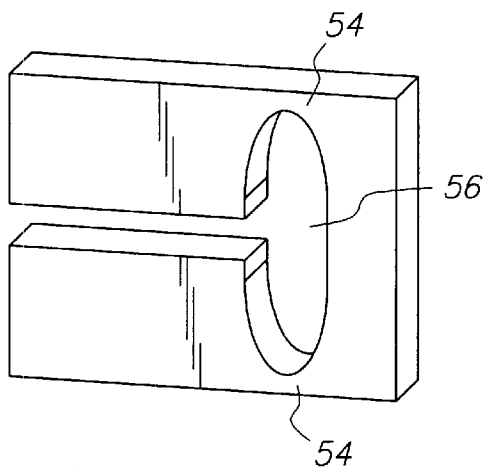

FIG. 3b shows a simple ductile hinge design that allows material strain to be limited to some specified level. The ductile hinge of FIG. 3b is formed by a rectangular circumferential groove 46 with filleted corners 48 on one side of a strut, the opposite side 50 of the strut remaining straight. The ductile hinges 44 are substantially rectangular sections between the ends of the groove 46 and the side walls 50.

One of the key concepts in FIG. 3b is that the ductile hinge 44 has a constant or substantially constant width along at least a portion of its total length. In this configuration, there is no local minimum width along the ductile hinge axis, as there is with pairs of concave roots. There is therefore no point concentration of stresses and strains along the length of the ductile hinge beam during stent expansion. In particular, maximum tensile and compressive strains will be distributed evenly along the upper and lower surfaces of the hinge 44 during stent expansion. With the gross bend angle limited by mechanical stops, which are described below in detail, the maximum material strain (at the hinge surfaces) can therefore be reliably limited by adjusting the initial length of the ductile hinge over which the total elongation is distributed.

Figure 3D:
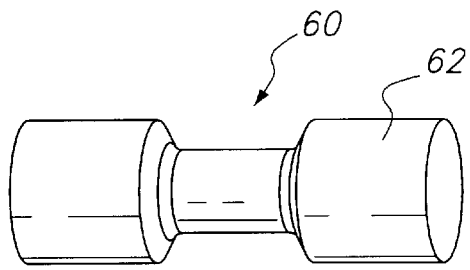

FIG. 3d shows a ductile hinge 60 in a cylindrical wire 62 for incorporating into a wire-form tissue-supporting device. The ductile hinge 60 is formed by a reduced diameter portion of the wire 62. Again, it is important that the ductile hinge have a substantially constant width over a portion of its length in order to provide strain control. Preferably, the ductile hinge is prismatic over a portion of its length. Maximum material strain can be varied by adjusting the hinge length. The ductile hinges of the present invention have a constant or substantially constant width over at least ⅓ of the ductile hinge length, and preferably over at least ½ of the ductile hinge length.

Figure 3E:
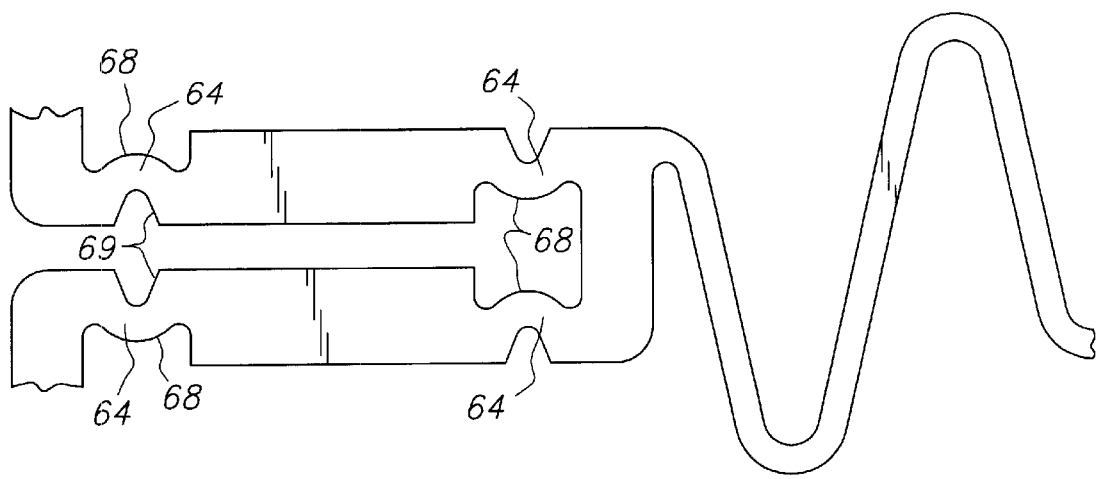
FIG. 3e is a side view of another embodiment of a ductile hinge.

FIG. 3e shows an asymmetric ductile hinge 63 that produces different strain versus deflection-angle functions in expansion and compression. Each of the ductile hinges 64 is formed between a convex surface 68 and a concave surface 69. The ductile hinge 64 according to a preferred embodiment essentially takes the form of a small, prismatic curved beam having a substantially constant cross section. However, a thickness of the curved ductile hinge 64 may vary somewhat as long as the ductile hinge width remains constant along a portion of the hinge length. The width of the curved beam is measured along the radius of curvature of the beam. This small curved beam is oriented such that the smaller concave surface 69 is placed in tension in the device crimping direction, while the larger convex surface 68 of the ductile hinges is placed in tension in the device expansion direction. Again, there is no local minimum width of the ductile hinge 64 along the (curved) ductile hinge axis, and no concentration of material strain. During device expansion tensile strain will be distributed along the convex surface 68 of the hinge 64 and maximum expansion will be limited by the angle of the walls of the concave notch 69 which provide a geometric deflection limiting feature. Maximum tensile strain can therefore be reliably limited by adjusting the initial length of the convex arc shaped ductile hinge 64 over which the total elongation is distributed.

The ductile hinges illustrated in FIGS. 3a–e are examples of different structures that will function as a stress/strain concentrator. Many other stress/strain concentrator configurations may also be used as the ductile hinges in the present invention. The ductile hinges according to the present invention generally include an abrupt change in width of a strut that functions to concentrate stresses and strains in the narrower section of the strut. These ductile hinges also generally include features to limit mechanical deflection of attached struts and features to control material strain during large strut deflections. Although the ductile hinges have been illustrated in FIG. 2 as positioned at the ends of each of the axial slots 22, they may also be positioned at other locations in other designs without departing from the present invention.

Figure 4A:
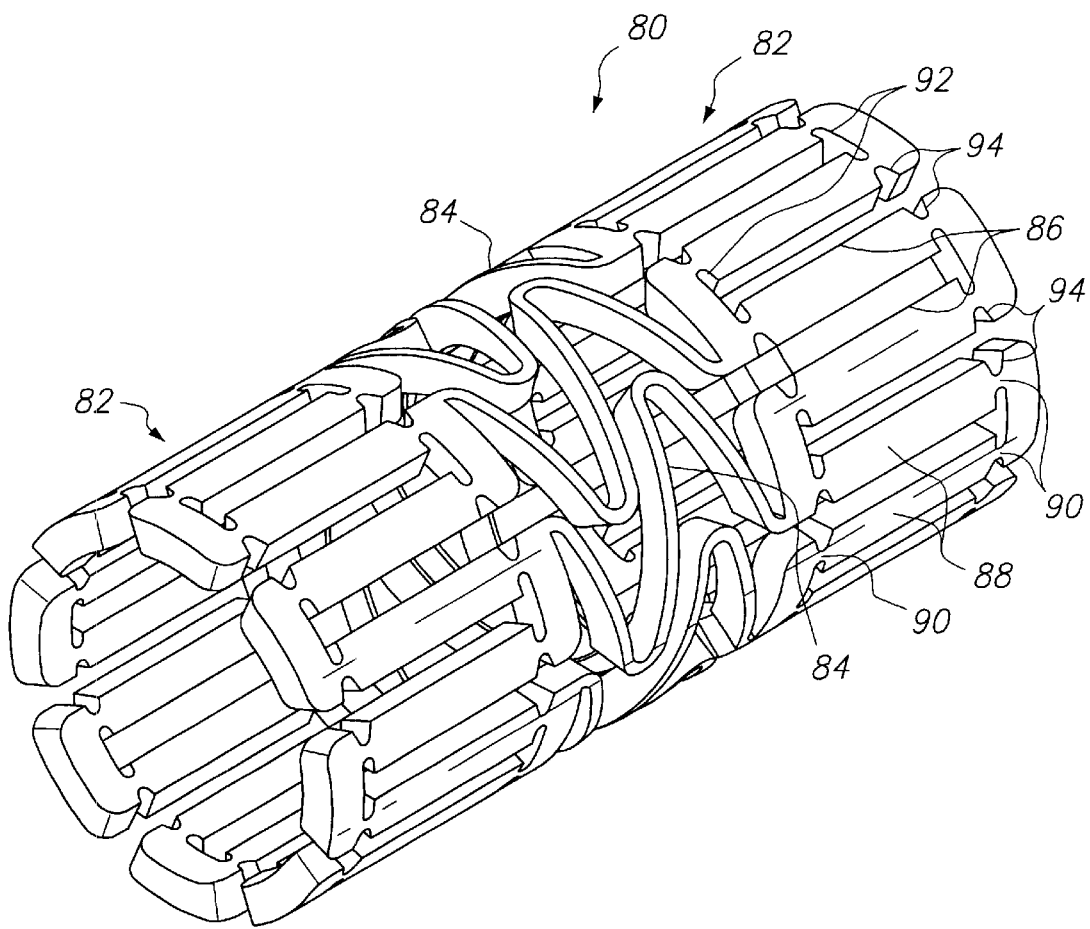
FIGS. 4a and 4b are an isometric view and an enlarged side view of a tissue-supporting device in accordance with an alternative embodiment of the invention.
Figure 4B:
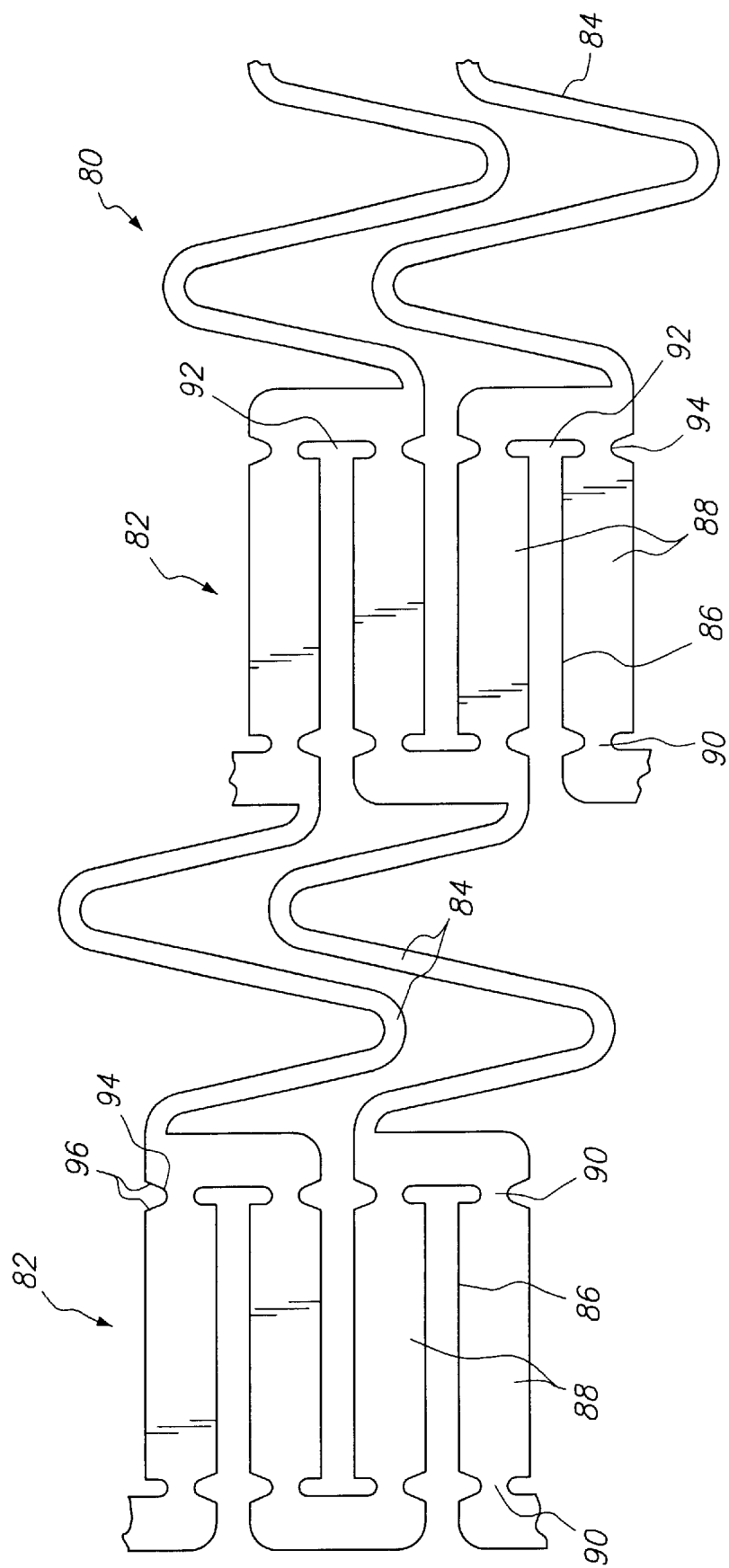

An alternative embodiment of a tissue supporting device 80 is illustrated in FIG. 4a and in the enlarged side view of FIG. 4b. The tissue supporting device 80 includes a plurality of cylindrical tubes 82 connected by S-shaped bridging elements 84. The bridging elements 84 allow the tissue supporting device to bend axially when passing through the tortuous path of the vasculature to the deployment site and allow the device to bend when necessary to match the curvature of a lumen to be supported. The S-shaped bridging elements 84 provide improved axial flexibility over prior art devices due to the thickness of the elements in the radial direction which allows the width of the elements to be relatively small without sacrificing radial strength. For example, the width of the bridging elements 84 may be about 0.0012–0.0013 inches (0.0305–0.0330 mm). Each of the cylindrical tubes 82 has a plurality of axial slots 86 extending from an end surface of the cylindrical tube toward an opposite end surface. A plurality of axial struts 88 having ductile hinges 90 are formed between the axial slots 86. The ductile hinges 90 are formed by circumferential slots 92 formed at the interior ends of the axial slots 86 and opposed notches 94.

The notches 94 each have two opposed angled walls 96 which function as a stop to limit geometric deflection of the ductile hinge, and thus limit maximum device expansion. As the cylindrical tubes 82 are expanded and bending occurs at the ductile hinges 90, the angled side walls 96 of the notches 94 move toward each other. Once the opposite side walls 96 of a notch come into contact with each other, they resist further expansion of the particular ductile hinge causing further expansion to occur at other sections of the tissue supporting device. This geometric deflection limiting feature is particularly useful where uneven expansion is caused by either variations in the tissue supporting device 80 due to manufacturing tolerances or uneven balloon expansion.

The tissue supporting device 20, 80 according to the present invention may be formed of any ductile material, such as steel, gold, silver, tantalum, titanium, Nitinol, other shape memory alloys, other metals, or even some plastics. One preferred method for making the tissue supporting device 20, 80 involves forming a cylindrical tube and then laser cutting the slots 22, 26, 86, 92 and notches 94 into the tube. Alternatively, the tissue supporting device may be formed by electromachining, chemical etching followed by rolling and welding, or any other known method.

The design and analysis of stress/strain concentration for ductile hinges, and stress/strain concentration features in general, is complex. For example, the stress concentration factor for the simplified ductile hinge geometry of FIG. 3a can be calculated and is given by the following expression where D is the width of the struts 28, h is the height of the circular grooves 38, 40, and r is the radius of curvature of the grooves. For purposes of this example the ratio of h/r is taken to be 4. However, other ratios of h/r can also be implemented successfully.

$$K = 4.935 - 7.586\left(\frac{2h}{D}\right) + 0.515\left(\frac{2h}{D}\right)^2 + 0.432\left(\frac{2h}{D}\right)^3$$

The stress concentration factors are generally useful only in the linear elastic range. Stress concentration patterns for a number of other geometries can be determined through photoelastic measurements and other experimental methods. Stent designs based on the use of stress/strain concentration features, or ductile hinges, generally involve more complex hinge geometries and operate in the non-linear elastic and plastic deformation regimes.

Figure 5A:
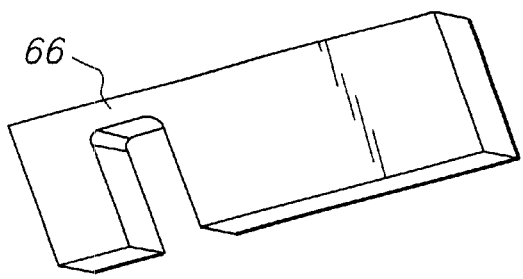
FIGS. 5a–5c are perspective, side, and cross-sectional views of an idealized ductile hinge for purposes of analysis.
Figure 5B:
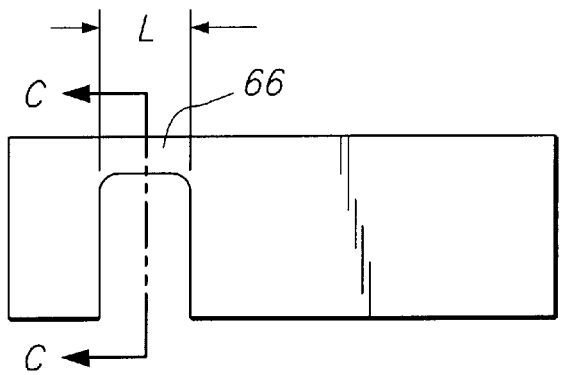
Figure 5C:
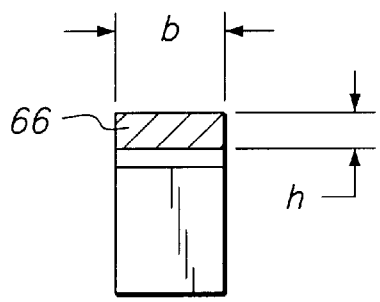
Figure 5D:
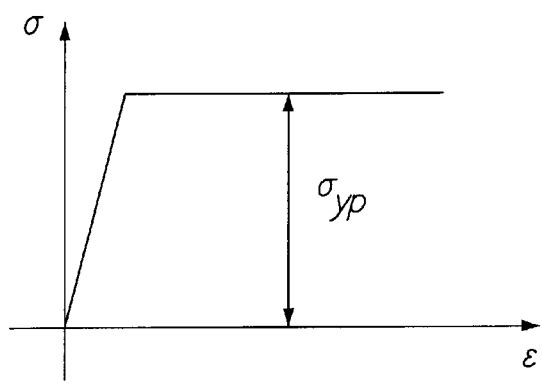
FIG. 5d is a stress/strain curve for the idealized ductile hinge.

The general nature of the relationship among applied forces, material properties, and ductile hinge geometry can be more easily understood through analysis of an idealized hinge 66 as shown in FIGS. 5a–5c. The hinge 66 is a simple beam of rectangular cross section having a width h, length L and thickness b. The idealized hinge 66 has elastic-ideally-plastic material properties which are characterized by the ideal stress/strain curve of FIG. 5d. It can be shown that the "plastic" or "ultimate bending moment" for such a beam is given by the expression:

$$M_P \equiv M_{ult} = \delta_{yp}\frac{bh^2}{4}$$

Where b corresponds to the cylindrical tube wall thickness, h is the circumferential width of the ductile hinge, and $\delta_{yp}$ is the yield stress of the hinge material. Assuming only that expansion pressure is proportional to the plastic moment, it can be seen that the required expansion pressure to expand the tissue supporting device increases linearly with wall thickness b and as the square of ductile hinge width h. It is thus possible to compensate for relatively large changes in wall thickness b with relatively small changes in hinge width h. While the above idealized case is only approximate, empirical measurements of expansion forces for different hinge widths in several different ductile hinge geometries have confirmed the general form of this relationship. Accordingly, for different ductile hinge geometries it is possible to increase the thickness of the tissue supporting device to achieve radiopacity while compensating for the increased thickness with a much smaller decrease in hinge width.

Ideally, the stent wall thickness b should be as thin as possible while still providing good visibility on a fluoroscope. For most stent materials, including stainless steel, this would suggest a thickness of about 0.005–0.007 inches (0.127–0.178 mm) or greater. The inclusion of ductile hinges in a stent design can lower expansion forces/pressures to very low levels for any material thickness of interest. Thus ductile hinges allow the construction of optimal wall thickness tissue supporting devices at expansion force levels significantly lower than current non-visible designs.

The expansion forces required to expand the tissue supporting device 20 according to the present invention from an initial condition illustrated in FIG. 2 to an expanded condition is between 1 and 5 atmospheres, preferably between 2 and 3 atmospheres. The expansion may be performed in a known manner, such as by inflation of a balloon or by a mandrel. The tissue supporting device 20 in the expanded condition has a diameter which is preferably up to three times the diameter of the device in the initial unexpanded condition.

Figure 6:
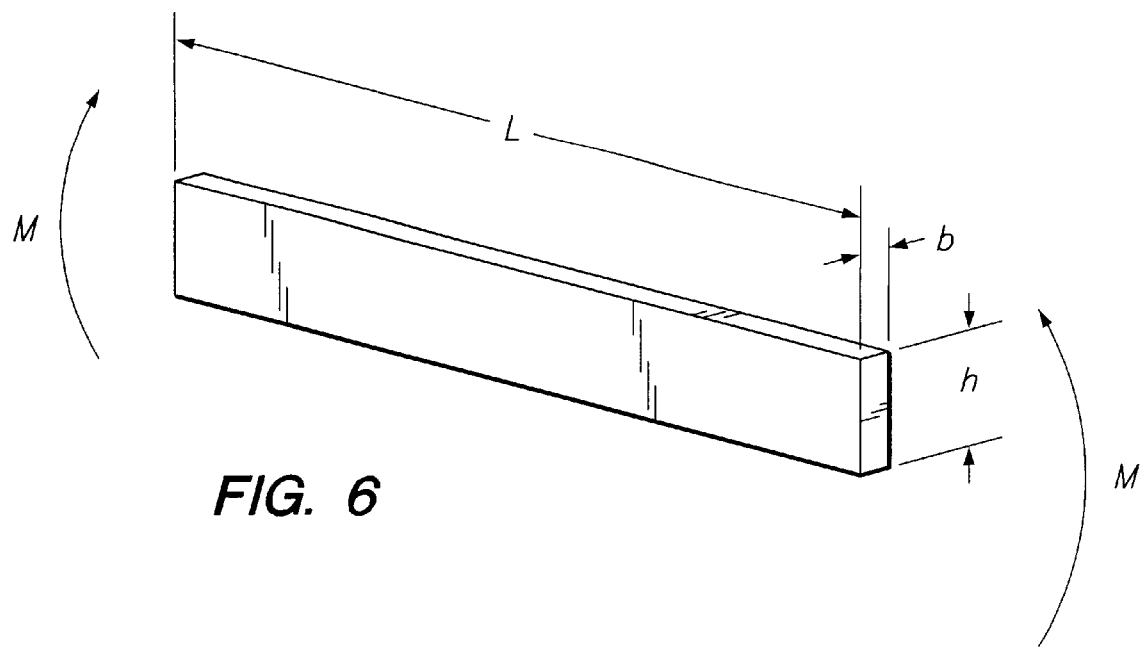
FIG. 6 is a perspective view of a simple beam for purposes of calculation.

Many tissue supporting devices fashioned from cylindrical tubes comprise networks of long, narrow, prismatic beams of essentially rectangular cross section as shown in FIG. 6. These beams which make up the known tissue supporting devices may be straight or curved, depending on the particular design. Known expandable tissue supporting devices have a typical wall thickness b of 0.0025 inches (0.0635 mm), and a typical strut width h of 0.005 to 0.006 inches (0.127–0.1524 mm). The ratio of b:h for most known designs is 1:2 or lower. As b decreases and as the beam length L increases, the beam is increasingly likely to respond to an applied bending moment M by buckling, and many designs of the prior art have displayed this behavior. This can be seen in the following expression for the "critical buckling moment" for the beam of FIG. 6.

$$M_{crit} = \frac{\pi b^3 h \sqrt{EG(1 - 0.63\, b/h)}}{6L}$$

Where:

E=Modulus of Elasticity

G=Shear Modulus

By contrast, in a ductile hinge based design according to the present invention, only the hinge itself deforms during expansion. The typical ductile hinge 32 is not a long narrow beam as are the struts in the known stents. Wall thickness of the present invention may be increased to 0.005 inches (0.127 mm) or greater, while hinge width is typically 0.002–0.003 inches (0.0508–0.0762 mm), preferably 0.0025 inches (0.0635 mm) or less. Typical hinge length, at 0.002 to 0.005 inches (0.0508–0.0127 mm), is more than an order of magnitude less than typical strut length. Thus, the ratio of b:h in a typical ductile hinge 32 is 2:1 or greater. This is an inherently stable ratio, meaning that the plastic moment for such a ductile hinge beam is much lower than the critical buckling moment $M_{crit}$, and the ductile hinge beam deforms through normal strain-curvature. Ductile hinges 32 are thus not vulnerable to buckling when subjected to bending moments during expansion of the tissue supporting device 20.

To provide optimal recoil and crush-strength properties, it is desirable to design the ductile hinges so that relatively large strains, and thus large curvatures, are imparted to the hinge during expansion of the tissue supporting device. Curvature is defined as the reciprocal of the radius of curvature of the neutral axis of a beam in pure bending. A larger curvature during expansion results in the elastic curvature of the hinge being a small fraction of the total hinge curvature. Thus, the gross elastic recoil of the tissue supporting device is a small fraction of the total change in circumference. It is generally possible to do this because common stent materials, such as 316L Stainless Steel have very large elongations-to-failure (i.e., they are very ductile).

It is not practical to derive exact expressions for residual curvatures for complex hinge geometries and real materials (i.e., materials with non-idealized stress/strain curves). The general nature of residual curvatures and recoil of a ductile hinge may be understood by examining the moment-curvature relationship for the elastic-ideally-plastic rectangular hinge 66 shown in FIGS. 5a–c. It may be shown that the relationship between the applied moment and the resulting beam curvature is:

$$M = M_p \left[ 1 - \frac{1}{3}\left(\frac{y_o}{h/2}\right)^2 \right] = 3/2 M_{yp} \left[ 1 - \frac{1}{3}\left(\frac{\kappa_{yp}}{\kappa}\right)^2 \right]$$

Figure 7:
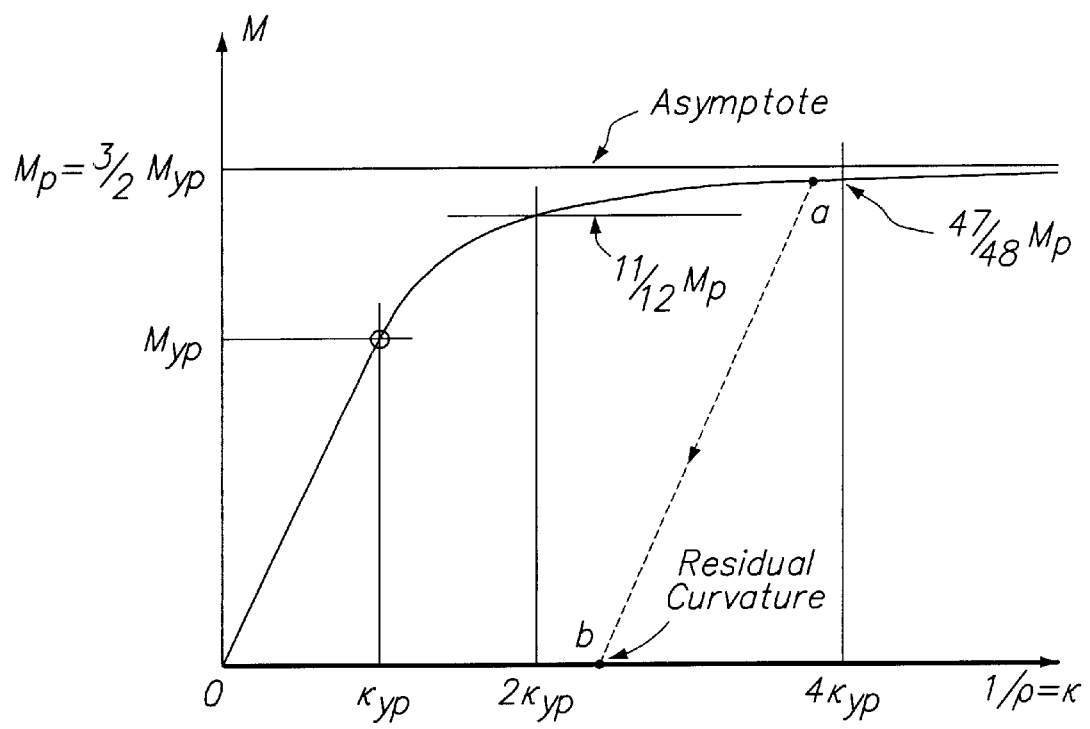
FIG. 7 is a moment verses curvature graph for a rectangular beam.

This function is plotted in FIG. 7. It may be seen in this plot that the applied moment M asymptotically approaches a limiting value $M_p$, called the plastic or ultimate moment. Beyond $^{11}/_{12} M_p$ large plastic deformations occur with little additional increase in applied moment. When the applied moment is removed, the beam rebounds elastically along a line such as a-b. Thus, the elastic portion of the total curvature approaches a limit of 3/2 the curvature at the yield point. These relations may be expressed as follows:

$$M_p = \frac{3}{2} M_{yp} \Rightarrow \kappa_{rebound} = \frac{3}{2} \kappa_{yp}$$

Imparting additional curvature in the plastic zone cannot further increase the elastic curvature, but will decrease the ratio of elastic to plastic curvature. Thus, additional curvature or larger expansion of the tissue supporting device will reduce the percentage recoil of the overall stent structure.

Figure 8:
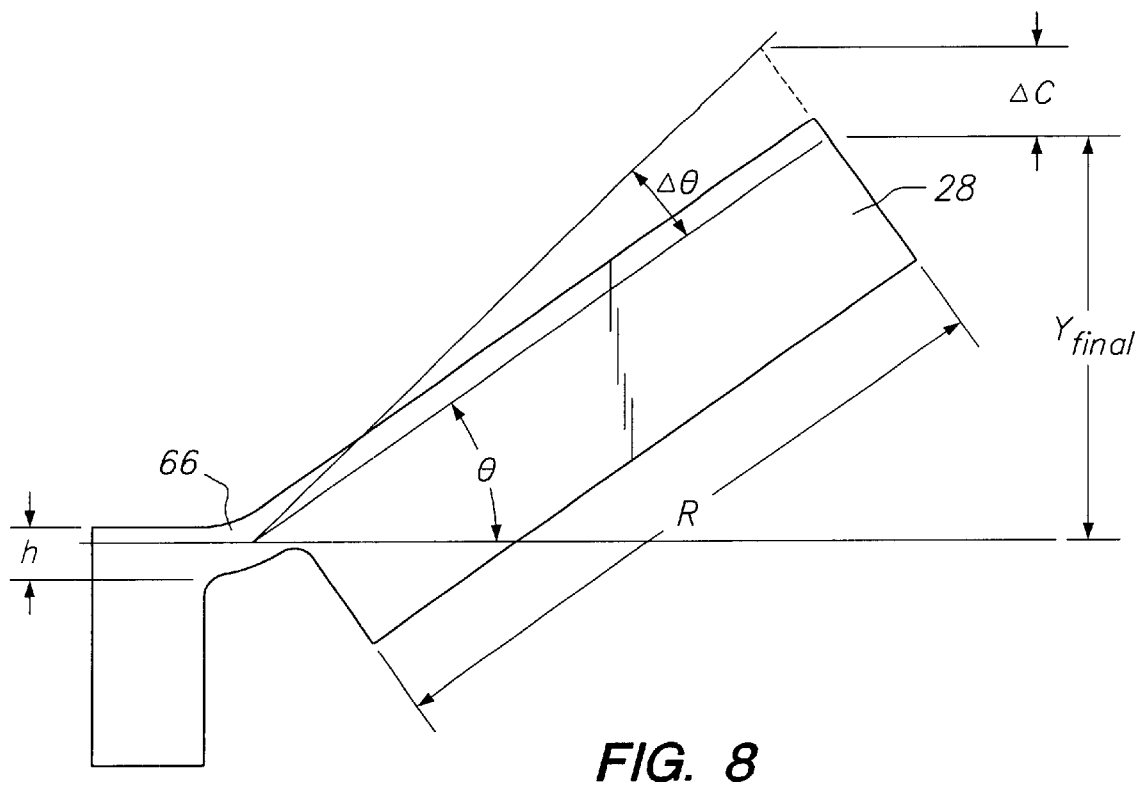
FIG. 8 is an enlarged side view of a bent ductile hinge.

As shown in FIG. 8, when a rigid strut 28 is linked to the ductile hinge 66 described above, the strut 28 forms an angle θ with the horizontal that is a function of hinge curvature. A change in hinge curvature results in a corresponding change in this angle θ. The angular elastic rebound of the hinge is the change in angle Δθ that results from the rebound in elastic curvature described above, and thus angular rebound also approaches a limiting value as plastic deformation proceeds. The following expression gives the limiting value of angular elastic rebound for the idealized hinge of FIG. 8.

$$\theta_{rebound} = 3\epsilon_{yp} \frac{L}{h}$$

Where strain at the yield point is an independent material property (yield stress divided by elastic modulus); L is the length of the ductile hinge; and h is the width of the hinge. For non-idealized ductile hinges made of real materials, the constant 3 in the above expression is replaced by a slowly rising function of total strain, but the effect of geometry would remain the same. Specifically, the elastic rebound angle of a ductile hinge decreases as the hinge width h increases, and increases as the hinge length L increases. To minimize recoil, therefore, hinge width h should be increased and length L should be decreased.

Ductile hinge width h will generally be determined by expansion force criteria, so it is important to reduce hinge length to a practical minimum in order to minimize elastic rebound. Empirical data on recoil for ductile hinges of different lengths show significantly lower recoil for shorter hinge lengths, in good agreement with the above analysis.

The ductile hinges 32 of the tissue supporting device 20 provide a second important advantage in minimizing device recoil. The embodiment of FIG. 2 shows a network of struts joined together through ductile hinges to form a cylinder. In this design, the struts 28 are initially parallel to an axis of the device. As the device is expanded, curvature is imparted to the hinges 32, and the struts 28 assume an angle θ with respect to their original orientation, as shown in FIG. 8. The total circumferential expansion of the tissue supporting device structure is a function of hinge curvature (strut angle) and strut length. Moreover, the incremental contribution to stent expansion (or recoil) for an individual strut depends on the instantaneous strut angle. Specifically, for an incremental change in strut angle Δθ, the incremental change in circumference ΔC will depend on the strut length R and the cosine of the strut angle θ.

$$\Delta C = R \, \Delta\theta \cos \theta$$

Since elastic rebound of hinge curvature is nearly constant at any gross curvature, the net contribution to circumferential recoil ΔC is lower at higher strut angles θ. The final device circumference is usually specified as some fixed value, so decreasing overall strut length can increase the final strut angle θ. Total stent recoil can thus be minimized with ductile hinges by using shorter struts and higher hinge curvatures when expanded.

Empirical measurements have shown that tissue supporting device designs based on ductile hinges, such as the embodiment of FIG. 2, display superior resistance to compressive forces once expanded despite their very low expansion force. This asymmetry between compressive and expansion forces may be due to a combination of factors including the geometry of the ductile hinge, the increased wall thickness, and increased work hardening due to higher strain levels.

According to one example of the tissue supporting device of the invention, the device can be expanded by application of an internal pressure of about 2 atmospheres or less, and once expanded to a diameter between 2 and 3 times the initial diameter can withstand a compressive force of about 16 to 20 gm/mm or greater. Examples of typical compression force values for prior art devices are 3.8 to 4.0 gm/mm.

While both recoil and crush strength properties of tissue supporting devices can be improved by use of ductile hinges with large curvatures in the expanded configuration, care must be taken not to exceed an acceptable maximum strain level for the material being used. For the ductile hinge 44 of FIG. 3b, for example, it may be shown that the maximum material strain for a given bend angle is given by the expression:

$$\epsilon_{max} = \frac{h}{L}\frac{\theta}{2}$$

Where $\epsilon_{max}$ is maximum strain, h is ductile hinge width, L is ductile hinge length and θ is bend angle in radians. When strain, hinge width and bend angle are determined through other criteria, this expression can be evaluated to determine the correct ductile hinge length L.

For example, suppose the ductile hinge 44 of FIG. 3b was to be fabricated of 316L stainless steel with a maximum strain of 30%; ductile hinge width h is set at 0.0025 inch (0.0635 mm) by expansion force criteria; and the bend angle θ is mechanically limited to 0.5 radians (≅30%) at full stent expansion. Solving the above expression for L gives the required ductile hinge length of at least about 0.0033 inches (0.0838 mm).

Similar expressions may be developed to determine required lengths for more complicated ductile hinge geometries, such as shown in FIG. 3e. Typical values for the prismatic portions of these curved ductile hinges range from about 0.002 to about 0.0035 inches (0.051–0.089 mm) in hinge width and about 0.002 to about 0.006 inches (0.051–0.152 mm) in hinge length. The tissue supporting device design of FIGS. 4a and 4b include a stop which limits the maximum geometric deflection at the ductile hinges by the design of the angled walls 96 of the notches 94.

In many designs of the prior art, circumferential expansion was accompanied by a significant contraction of the axial length of the stent which may be up to 15% of the initial device length. Excessive axial contraction can cause a number of problems in device deployment and performance including difficulty in proper placement and tissue damage. Designs based on ductile hinges 32 can minimize the axial contraction, or foreshortening, of a tissue supporting device during expansion as follows.

Figure 9A:
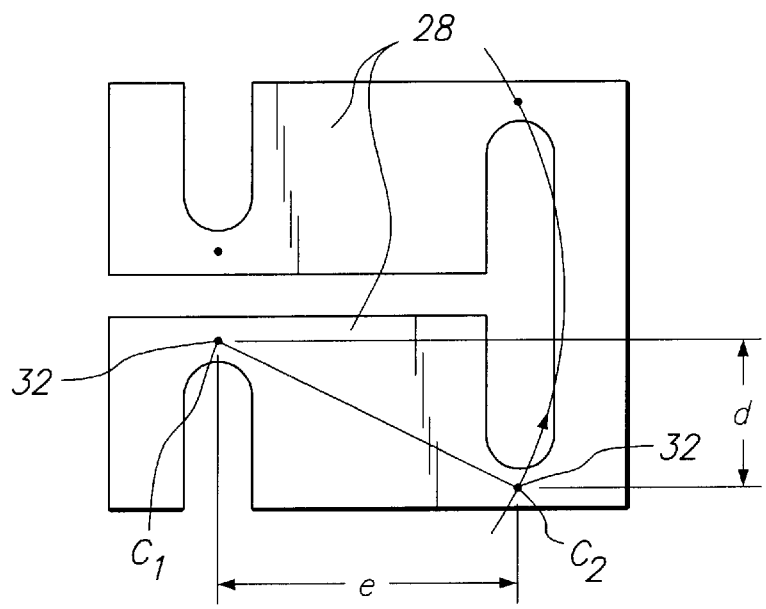
FIGS. 9a and 9b are enlarged side views of ductile hinges in initial and expanded positions with shortened struts to illustrate axial contraction relationships.
Figure 9B:
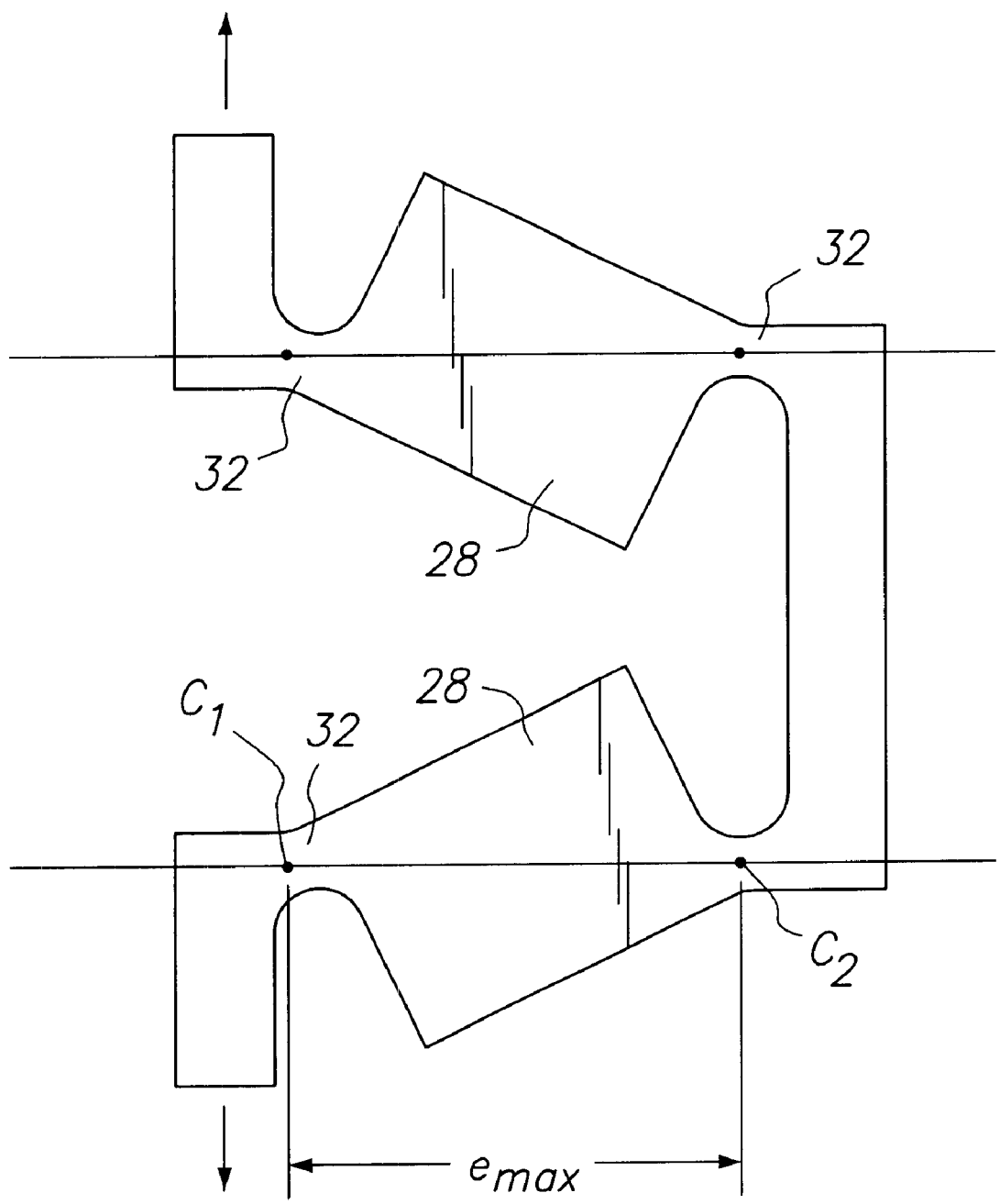

FIGS. 9a and 9b illustrate an exaggerated ductile hinge 32 and shortened struts 28 in initial and expanded conditions. Each strut 28 is attached to two ductile hinges 32 at opposite ends. Each ductile hinge 32 has an instant center of rotation $C_1$, $C_2$ that is an effective pivot point for the attached strut 28. Initially, during expansion the pivot point $C_1$ is displaced vertically by a distance d until $C_1$ is positioned even with $C_2$ as shown in FIG. 9b. When the array is expanded vertically, the axial struts 28 move in a circular arc with respect to the pivot points, as shown in FIG. 9b. It can be seen that the horizontal distance e between pivot points $C_1$ and $C_2$ actually increases initially, reaching a maximum $e_{max}$ when the two points are on the same horizontal axis as shown in FIG. 9b. As the vertical expansion continues, the device compresses axially back to its original length. Only when vertical expansion of the array continues beyond the point where the horizontal distance e between $C_1$ and $C_2$ is the same as the original horizontal distance e does the overall length of the array actually begin to contract. For the stent shown in FIG. 2, for example, approximately ⅓ of the total circumferential expansion has been accomplished by the time the configuration of FIG. 9b is reached, and the stent exhibits very low axial contraction.

This ability to control axial contraction based on hinge and strut design provides great design flexibility when using ductile hinges. For example, a stent could be designed with zero axial contraction.

Figure 10:
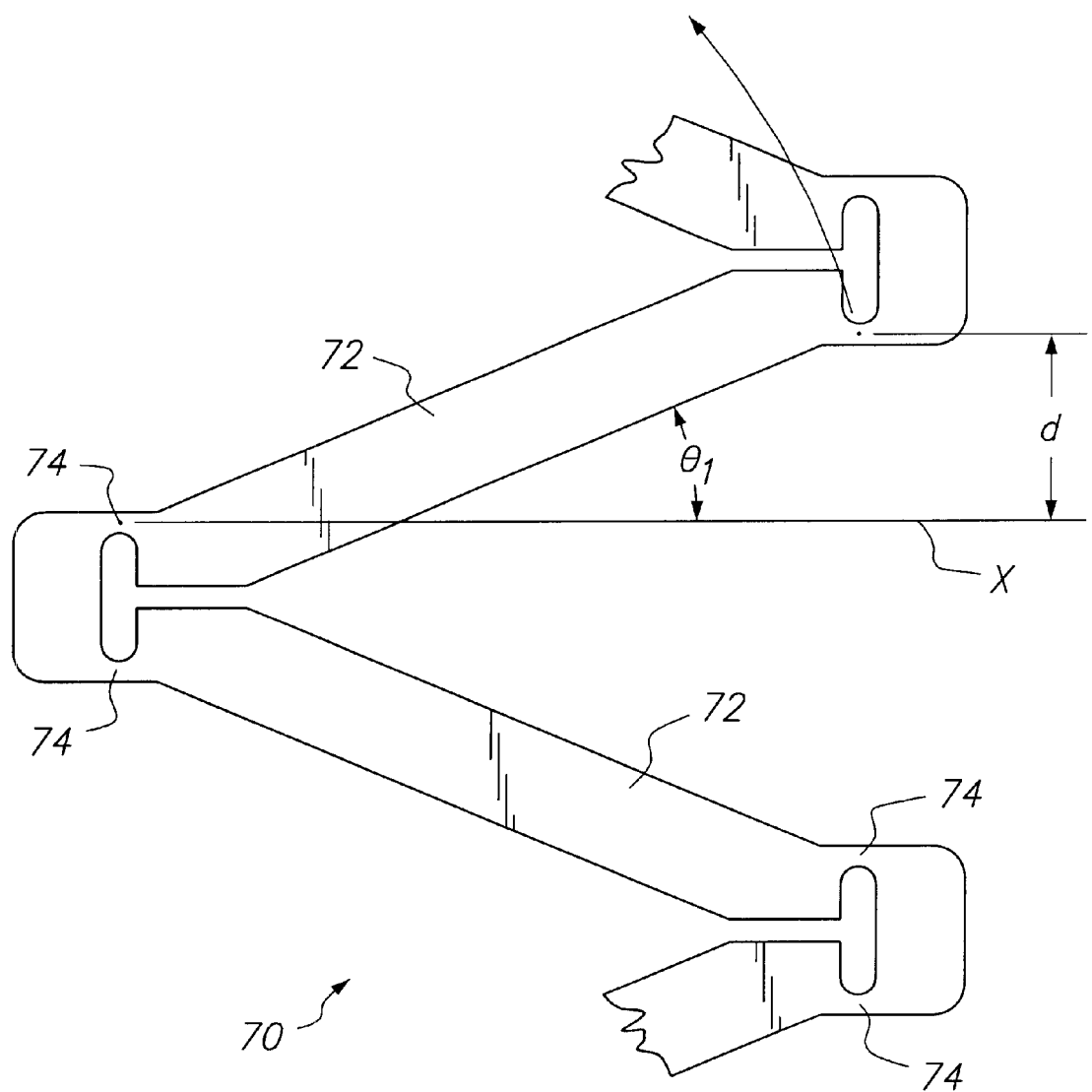
FIG. 10 is a side view of a portion of an alternative embodiment of a tissue supporting device having a high-crush-strength and low-recoil.

An alternative embodiment that illustrates the trade off between crush strength and axial contraction is shown in FIG. 10. FIG. 10 shows a portion of a tissue supporting device 70 having an array of struts 72 and ductile hinges 74 in the unexpanded state. The struts 72 are positioned initially at an angle $\theta_1$ with respect to a longitudinal axis X of the device. As the device is expanded radially from the unexpanded state illustrated in FIG. 10, the angle $\theta_1$ increases. In this case the device contracts axially from the onset of vertical expansion throughout the expansion. Once the device has been completely expanded the final angle $\theta_1$ made by the strut 72 with the horizontal will be much greater than the angle θ in the device of FIGS. 8a and 8b. As shown previously, a higher final strut angle $\theta_1$, can significantly increase crush strength and decrease circumferential recoil of the stent structure. However, there is a trade off between increased crush strength and increase in axial contraction.

According to one example of the present invention, the struts 72 are positioned initially at an angle of about 0° to 45° with respect to a longitudinal axis of the device. As the device is expanded radially from the unexpanded state illustrated in FIG. 10a, the strut angle increases to about 20° to 80°.

Tissue supporting devices including ductile hinges as described above can be used to create many useful device configurations in addition to the substantially cylindrical devices described above. For example, tissue supporting devices having ductile hinges may be designed in which various sections or areas of the device open at differential expansion pressures by varying the hinge configuration. This feature makes it possible to control the expansion sequence of different features and areas of the device. Another tissue supporting device design variation allows the creation of specially shaped side-access holes in the device which open up as the device expands and can be used accommodate vessel bifurcations.

Ductile hinges are especially useful in creating tissue supporting devices that expand in a specified sequence. By varying the width of specific ductile hinges in different areas of the tissue supporting device, the expansion pressure of each of the different areas of the device can be adjusted independently. As the device is expanded, such as by increasing pressure within a balloon, areas with the smallest hinge width open first, followed by expansion of areas with progressively wider hinge widths. A method of delivering an expandable medical device employing controlled expansion of the device is described in U.S. patent application Ser. No. 09/315,885, filed on even date herewith which is incorporated herein by reference in its entirety.

Figure 11A:
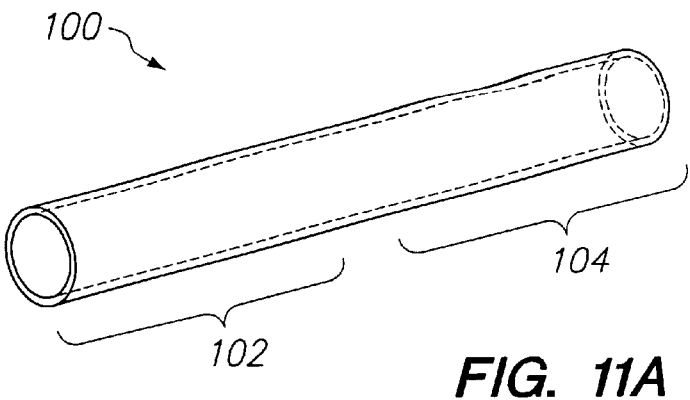
FIGS. 11a–11c are schematic side views of unexpanded, partially expanded, and fully expanded views of a differentially expanding tissue supporting device.
Figure 11B:
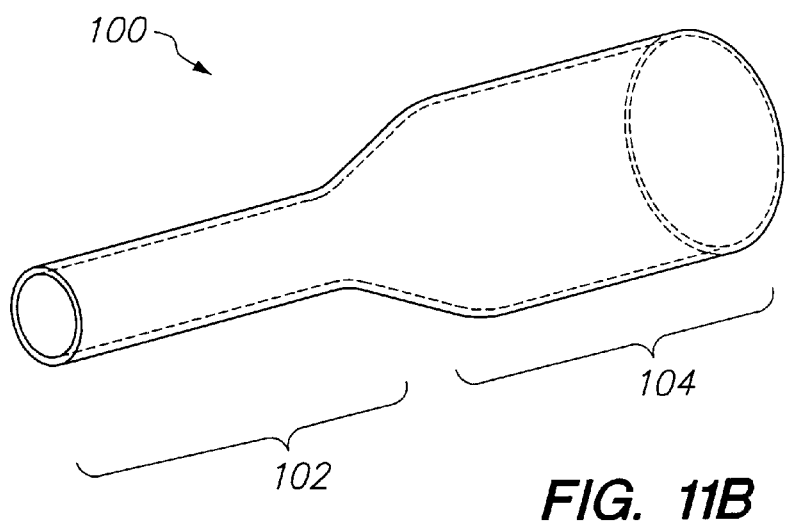
Figure 11C:
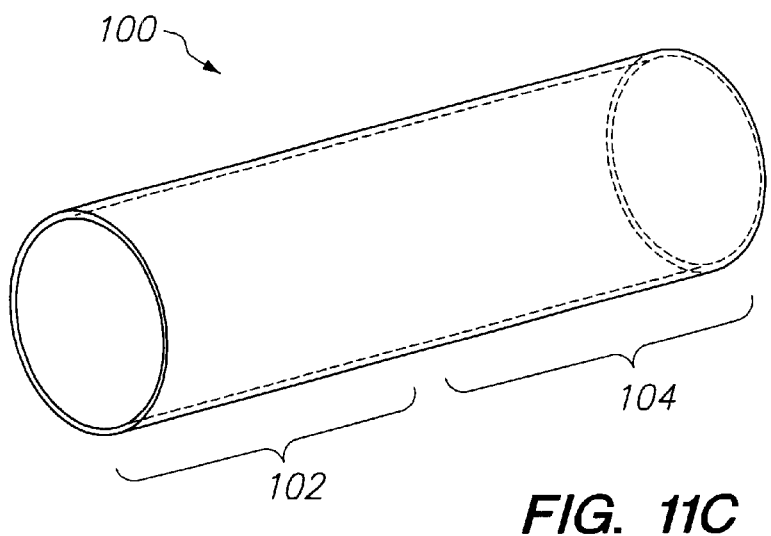

FIGS. 11a–11c show the sequence of expansion of a differentially expanding tissue supporting device 100 according to one embodiment of the invention. FIG. 11a shows an unexpanded tissue supporting device 100 in which a left portion 102 of the device has ductile hinges with larger hinge widths than a right portion 104 of the device. For example, the two left rows of struts of the device may have larger hinge widths than the two right rows of struts on the same device. Although the hinges in different sections 102, 104 of the device 100 have been described as having differing widths for achieving the desired differential expansion, the hinge geometry may alternatively be modified in other ways to achieve differential expansion.

To expand the device 100, a balloon or other expansion device is inserted into the central lumen of the device and the balloon is inflated. As the inflation pressure of the balloon is increased, the right side 104 of the device expands as shown in FIG. 11b. At this point, expansion can be halted with one half of the device expanded and the other unexpanded. The expansion may be halted to perform some other task such as removal of a locating device or for other reasons. Pressurization of the balloon is then continued to complete deployment of the left side 102 of the device as shown in FIG. 11c. Many more complex sequences of expansion are possible and potentially useful. For example, three or more segments of the device may be expanded at different times. Alternatively, the sections of the device which are differentially expanded may be cylindrical sections, longitudinal sections, rectangular sections, or sections of any other shape. Differential expansion is very useful in special deployment situations, such as treatment of bifurcations, and in creating special tissue supporting device features, such as side access holes as shown in FIGS. 12a–12c.

Figure 12A:
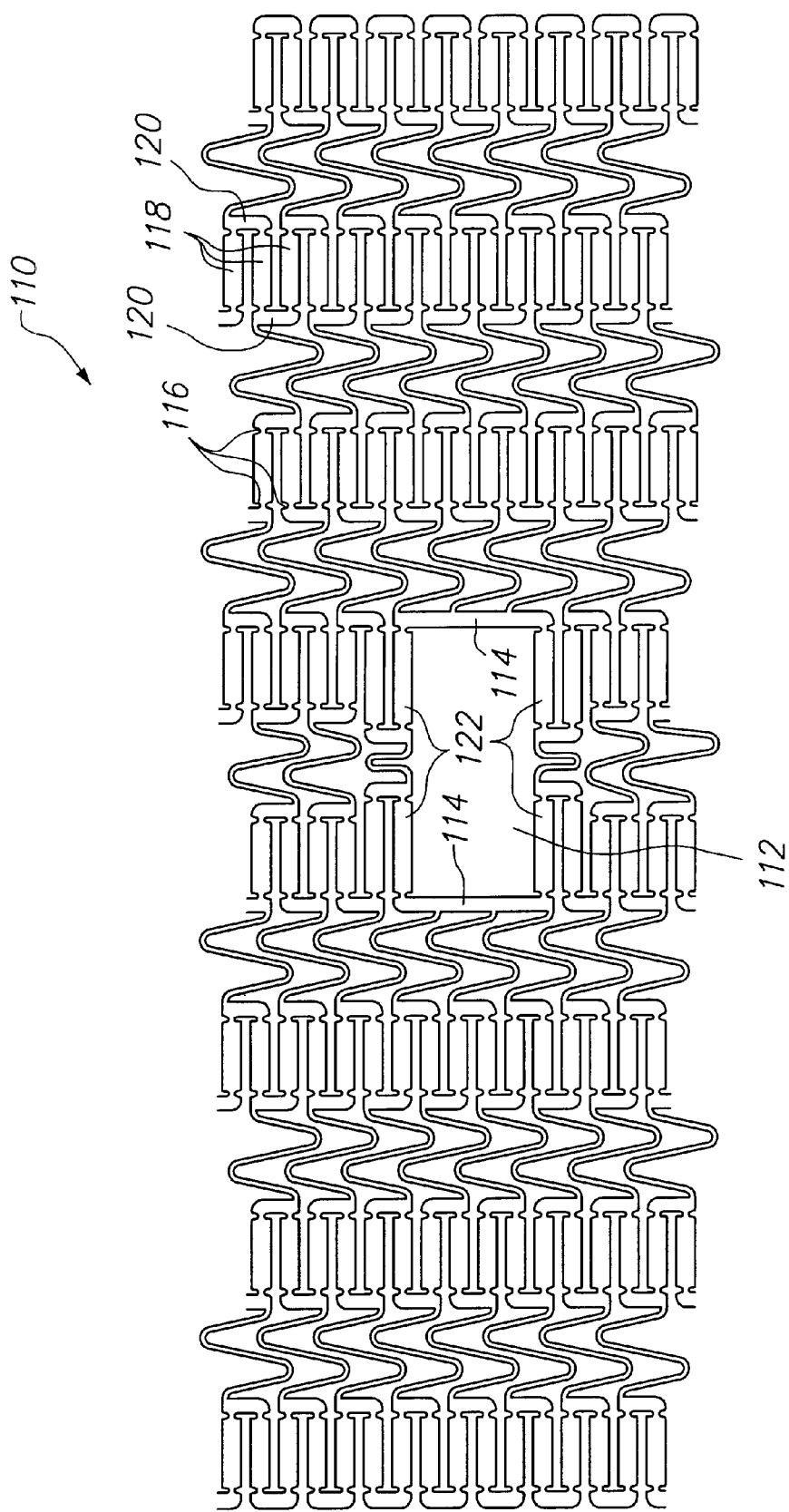
FIG. 12a is an unexpanded side view of a cylindrical tissue supporting device with a side hole feature, which has been laid flat for ease of illustration.
Figure 12B:
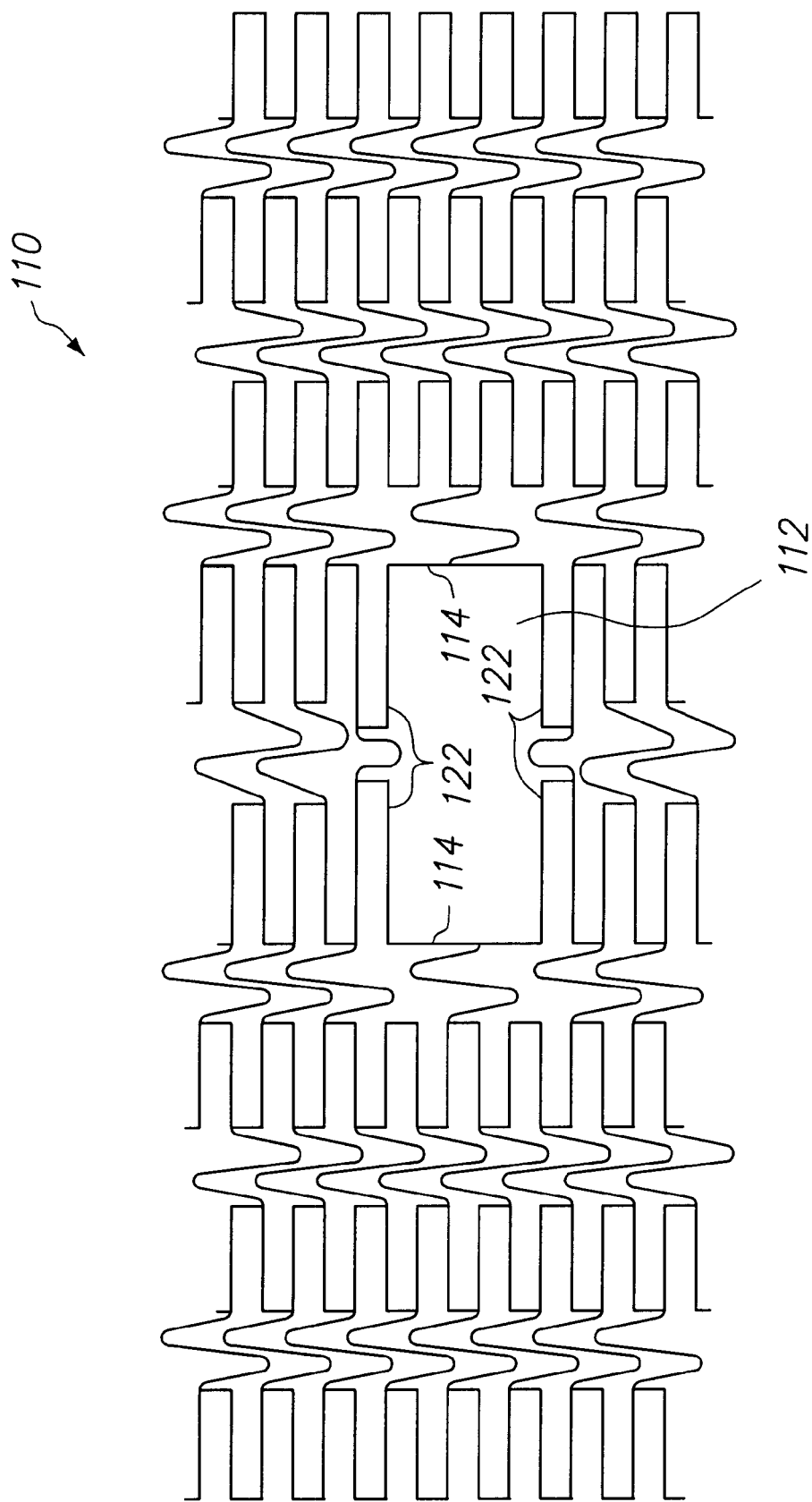
Figure 12C:
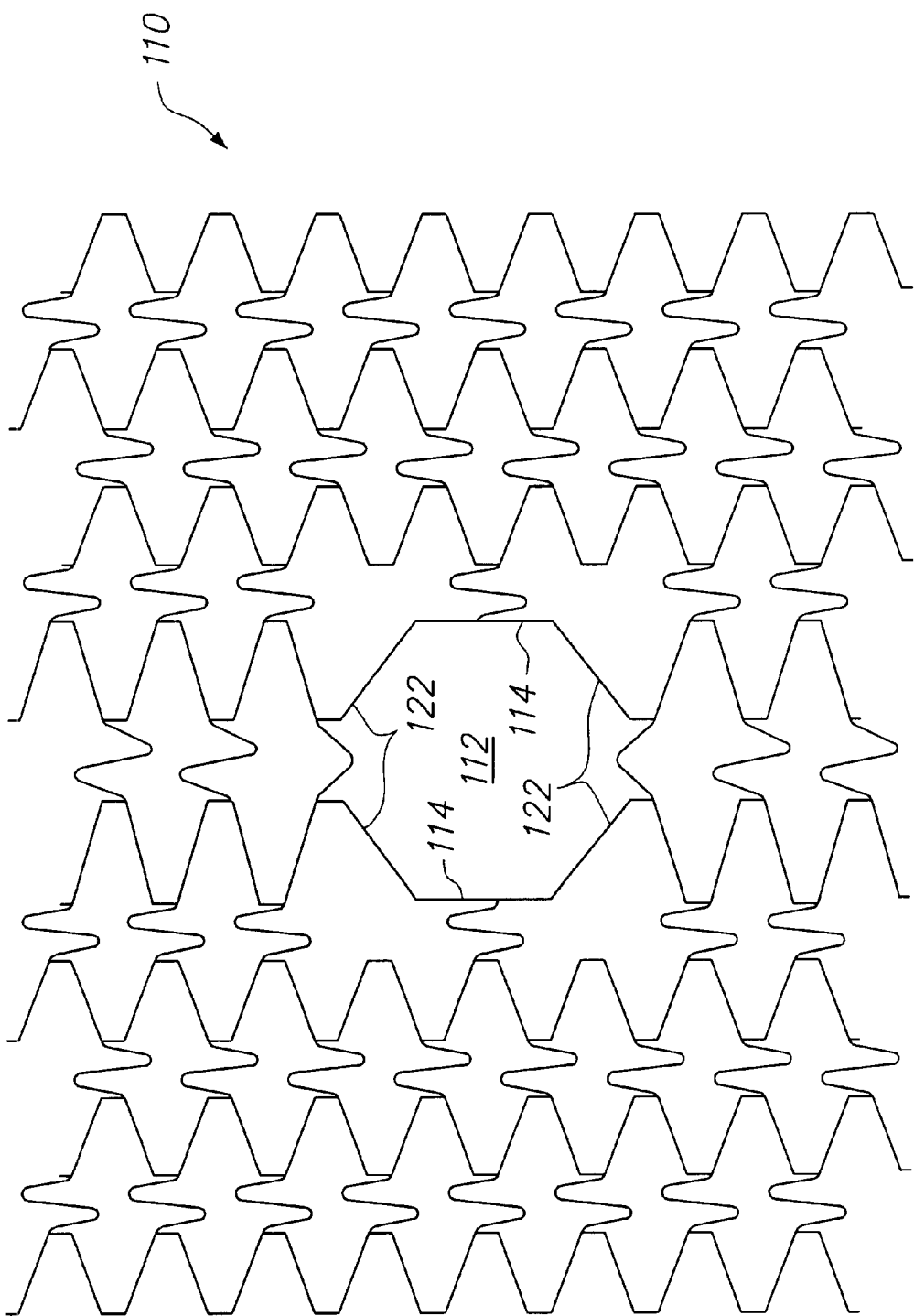

A framed hole feature, such as the feature shown in FIGS. 12a–12c, is capable of providing strong, uniform support to the tissue at a bifurcation in an artery. Known techniques for treating bifurcations generally deliver a mesh tissue supporting device into the artery and position the device over the bifurcation. According to the known methods, a surgeon then attempts to create one or more branch lumen access holes by inserting a balloon through the sidewall of the mesh device, and then inflating the balloon to simply push the local features of the mesh device aside. These techniques are inherently random in nature: the exact point of expansion in the device lattice cannot be predicted, and the device may or may not expand satisfactorily at that point. Tissue support provided by these known techniques for treating bifurcated arteries is similarly unpredictable.

FIG. 12a shows an unexpanded tissue support device 110 in which a rectangular hole 112 has been formed in the center. Ductile hinges 116 connect all the struts 118 and links 120 of the device as described above with respect to the previous embodiments. The ends of the device 110 have a regular pattern of struts 118 and ductile hinges 116. The hole 112 is formed by removing several axial struts and connecting their respective side links into two longer circumferential side links 114, which provide a vertical frame for the hole 112. The struts 122 which frame the hole 112 and connect the side links 114 may be straight, as shown, rounded, or contoured in some other way, depending on the desired final shape of the expanded hole feature.

According to one alternative embodiment of the invention, the ductile hinges 116 connecting the frame struts 122 and the side links 114 will be designed to open at a somewhat lower inflation pressure than the remainder of the ductile hinges around the rest of the circumference of the device. Thus, when the device 110 is expanded the struts 122 and side links 114 that frame the hole feature 112 will open first. When these struts 122 reach their maximum angle, defined by the hinge angles, the frame surrounding the hole 112 "locks" in its desired shape. The remaining struts 118 around the circumference of the device then expand in a normal fashion, providing full strength and support to the lumen opposite the hole 112. FIGS. 12b and 12c show schematic representations of the device of FIG. 12a in unexpanded and expanded configurations. As shown in FIG. 12c, the rectangular unexpanded hole feature 112 expands into an octagon shape.

A second property of ductile hinges is important in the creation of the side hole features 112. In applications requiring larger side holes, the expanded side hole may span less of the circumference of the expanded stent than the struts that were removed to create the hole. For this reason, the remaining struts in the rows containing the hole feature must span a larger portion of the circumference of the device. To do this, they must assume a greater bend angle, often as high as 60 degrees. This is easily accomplished with ductile hinges such as the one shown in FIG. 3e by increasing the arc length of the hinge.

The hole features according to the present invention may take on different shapes and sizes depending on the application. The framed-hole features can also be designed to take advantage of the superior crimping properties of ductile hinges. For example, ancillary devices can be crimped into a stenticatheter assembly in specially designed holes.

According to one alternative embodiment of the present invention, the expandable tissue supporting device can also be used as a delivery device for certain beneficial agents including drugs, chemotherapy, or other agents. Due to the structure of the tissue supporting device incorporating ductile hinges, the widths of the struts can be substantially larger than the struts of the prior art devices. The struts due to their large size can be used for beneficial agent delivery by providing beneficial agent on the struts or within the struts. Examples of beneficial agent delivery mechanisms include coatings on the struts, such as polymer coatings containing beneficial agents, laser drilled holes in the struts containing beneficial agent, and the like.

While the invention has been described in detail with reference to the preferred embodiments thereof, it will be apparent to one skilled in the art that various changes and modifications can be made and equivalents employed, without departing from the present invention.

What is claimed is:

1. A method of expanding a medical device comprising:
    providing a substantially cylindrical expandable medical device having a first section at a first end of the device with ductile hinges of a first configuration and a second section at a second end of the device with ductile hinges of a second configuration, wherein the second end requires a different force for expansion than the first end; and expanding the device in a controlled expansion sequence with an expandable member.

2. The method according to claim 1, wherein the hinges having the first configuration have a first hinge width which is smaller than a second hinge width of the hinges having the second configuration.

3. The method according to claim 1, wherein the first section is expanded prior to expansion of the second section.

4. The method according to claim 1, wherein the expansion is performed by inflating a balloon inside the cylindrical device.

5. The method according to claim 1, wherein the expansion of the first section is performed by inflating a balloon inside the cylindrical device to a first pressure and the expansion of the second section is performed by inflating the balloon to a second pressure.

6. The method according to claim 1, wherein the medical device is expanded within a body passage.

7. The method according to claim 1, wherein the step of expanding the device in a controlled expansion sequence includes limiting a total expansion with a geometric deflection limiting feature.

8. The method according to claim 1, wherein the step of expanding comprises expanding the first section to contact a bodily lumen followed by expanding the second section to contact the bodily lumen.

9. The method according to claim 1, wherein all the hinges located in the first section have the first configuration and all the hinges located in the second section have the second configuration.

10. A method of expanding a medical device comprising:
providing a substantially cylindrical expandable medical device having a first section surrounding a side access hole for accommodating vessel bifurcations with ductile hinges of a first configuration and a second section around a remainder of a circumference of the device with ductile hinges of a second configuration which require a different force for expansion than the first hinges; and expanding the device in a controlled expansion sequence with an expandable member.

11. The method according to claim 10, wherein the first section is expanded prior to expansion of the second section.

12. The method according to claim 11, wherein the hinges having the first configuration have a first hinge width which is smaller than a second hinge width of the hinges having the second configuration.

13. The method according to claim 10, wherein the hinges having the first configuration have a first hinge width which is smaller than a second hinge width of the hinges having the second configuration.

14. The method according to claim 10, wherein the expansion is performed by inflating a balloon inside the cylindrical device.

15. The method according to claim 10, wherein the step of expanding comprises expanding the first section to contact a bodily lumen followed by expanding the second section to contact the bodily lumen.

16. A method of expanding a medical device comprising:
providing a substantially cylindrical expandable medical device having a first annular section of the device with ductile hinges of a first configuration and a second annular section of the device with ductile hinges of a second configuration, wherein the second section is longitudinally displaced from the first section and requires a different force for expansion than the first section; and expanding the device in a controlled expansion sequence with an expandable member.

17. The method according to claim 16, wherein the hinges having the first configuration have a first hinge width which is smaller than a second hinge width of the hinges having the second configuration.

18. The method according to claim 16, wherein the expansion is performed by inflating a balloon inside the cylindrical device.

19. The method according to claim 16, wherein the step of expanding comprises expanding the first section to contact a bodily lumen followed by expanding the second section to contact the bodily lumen.

* * * * *